(12) United States Patent
Brinkmann et al.

(10) Patent No.: US 9,180,193 B2
(45) Date of Patent: Nov. 10, 2015

(54) ANTIVIRAL COMPOUNDS

(71) Applicant: Hoffmann-La Roche Inc., Nutley, NJ (US)

(72) Inventors: John A. Brinkmann, West Caldwell, NJ (US); Hongju Li, Edison, NJ (US); Ramakanth Sarabu, Towaco, NJ (US); Sung-Sau So, Verona, NJ (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/351,029

(22) PCT Filed: Oct. 8, 2012

(86) PCT No.: PCT/EP2012/069811
§ 371 (c)(1),
(2) Date: Apr. 10, 2014

(87) PCT Pub. No.: WO2013/053657
PCT Pub. Date: Apr. 18, 2013

(65) Prior Publication Data
US 2014/0255344 A1 Sep. 11, 2014

Related U.S. Application Data

(60) Provisional application No. 61/545,216, filed on Oct. 10, 2011.

(51) Int. Cl.
C07D 487/04 (2006.01)
C07D 519/00 (2006.01)
A61K 45/06 (2006.01)
A61K 31/551 (2006.01)

(52) U.S. Cl.
CPC .............. A61K 45/06 (2013.01); A61K 31/551 (2013.01); C07D 487/04 (2013.01); C07D 519/00 (2013.01)

(58) Field of Classification Search
CPC ..................... C07D 487/04; C07D 519/00
See application file for complete search history.

(56) References Cited

U.S. PATENT DOCUMENTS 5,552,400 A * 9/1996 Dolle et al. .................. 514/221

* cited by examiner

Primary Examiner — Bruck Kifle

(57) ABSTRACT

The present invention discloses compounds of Formulae I and II, wherein the variables in Formulae I and II are defined as described herein. Also disclosed are pharmaceutical compositions containing such compounds and methods for using the compounds of Formulae I and II in the treatment of HCV infection.

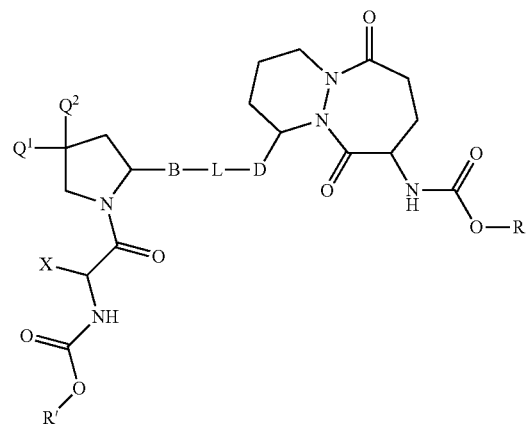

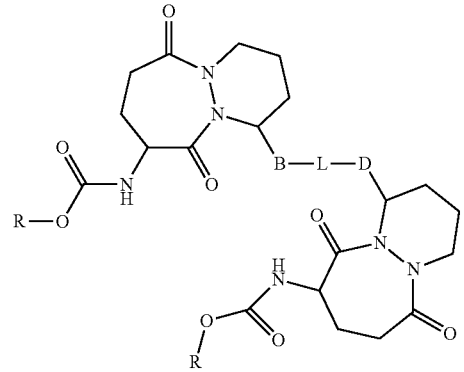

36 Claims, No Drawings

ANTIVIRAL COMPOUNDS

This application is a National Stage Application of PCT/EP2012/069811 filed Oct. 8, 2012, which claims priority from Provisional Patent Application No. 61/545,216 filed on Oct. 10, 2011. Each of these applications is hereby incorporated by reference herein in its entirety.

The present invention provides non-nucleoside compounds of Formulae I or II useful as inhibitors of hepatitis C virus (HCV), as inhibitors of HCV replication, and for the treatment of hepatitis C infection.

Hepatitis C virus (HCV) infection is a major health problem that leads to chronic liver disease, such as cirrhosis and hepatocellular carcinoma, in a substantial number of infected individuals. Current treatments for HCV infection include immunotherapy with recombinant interferon-α alone or in combination with the nucleoside-analog ribavirin.

Several virally-encoded enzymes are putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NS5B).

One identified target for therapeutic intervention is HCV NS5A non-structural protein. A non-structural protein, NS5A is an essential component for viral replication and assembly. Mutations in NS5A at or near known sites of phosphorylation can affect the ability for high-level replication in cell-culture systems, suggesting an important role for NS5A phosphorylation in viral replication efficiency. Inhibitors of the phosphorylation of NS5A can lead to reduced viral RNA replication.

There is a clear and long-felt need to develop effective therapeutics for treatment of HCV infection. Specifically, there is a need to develop compounds that are useful for treating HCV-infected patients and compounds that selectively inhibit HCV viral replication.

The application provides a compound of Formula I or II:

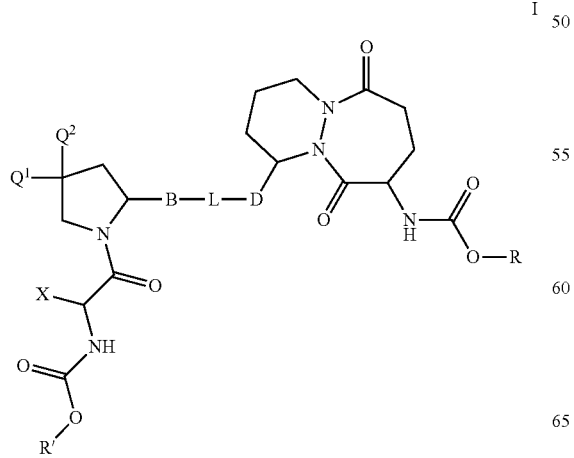

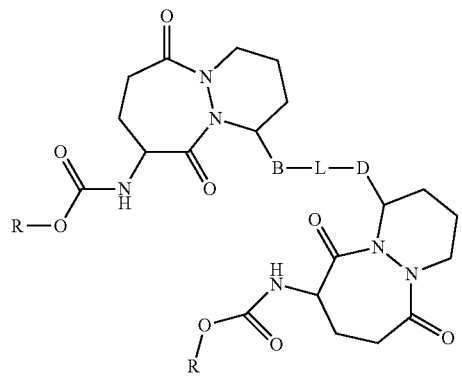

wherein:

X is lower alkyl;

each R is lower alkyl, or benzyl;

each R' is lower alkyl;

B and D are independently selected from the group consisting of

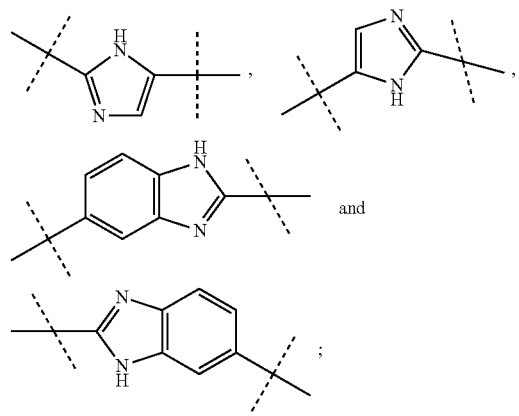

$Q^1$ and $Q^2$ are independently H or F;

or $Q^1$ and $Q^2$ together form heterocycloalkyl; and

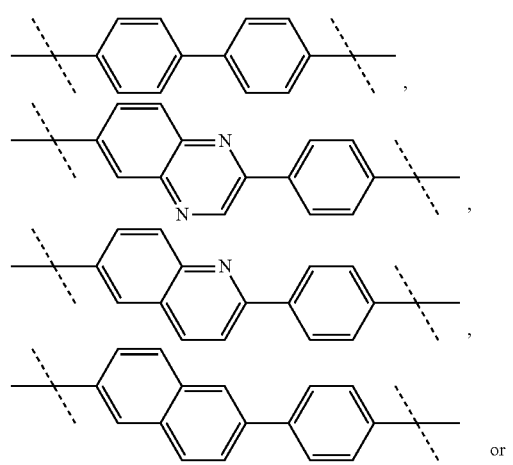

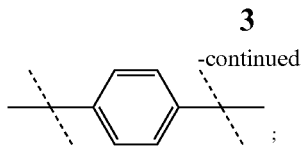

L is or a pharmaceutically acceptable salt thereof.

The application provides a method for treating a Hepatitis C Virus (HCV) infection comprising administering to a patient in need thereof a therapeutically effective amount of a compound of Formula I or II.

The application provides a composition comprising a compound of Formula I or II and a pharmaceutically acceptable excipient.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "- - - - - -" drawn through a bond each refer to the point of attachment of a functional group or other chemical moiety to the rest of the molecule of which it is a part. Thus, for example:

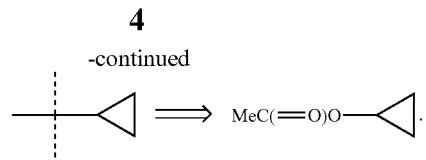

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include ketoenol (—C(=O)—CH— ⇌ —C(—OH)=CH—), amideimidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro[3.3]heptane. The term spiroheterocycloalkyl, as used herein, means a spirocyclic heterocycloalkyl, such as, for example, 2,6-diaza spiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "PCy$_3$" refers to a phosphine trisubstituted with three cyclic moieties.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term carboxy-alkyl as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a CO$_2$H moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N, O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

The application provides a compound of Formula I or II:

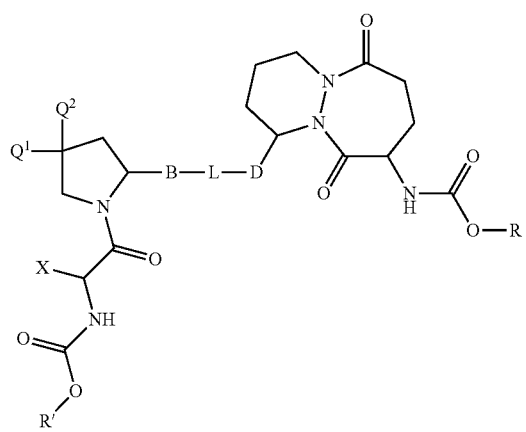

I

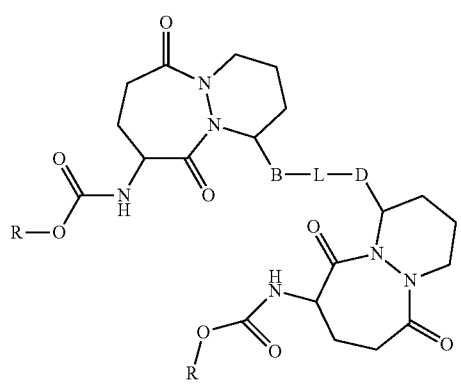

II wherein:

X is lower alkyl;

each R is independently lower alkyl, or benzyl;

each R' is lower alkyl;

B and D are independently selected from the group consisting of

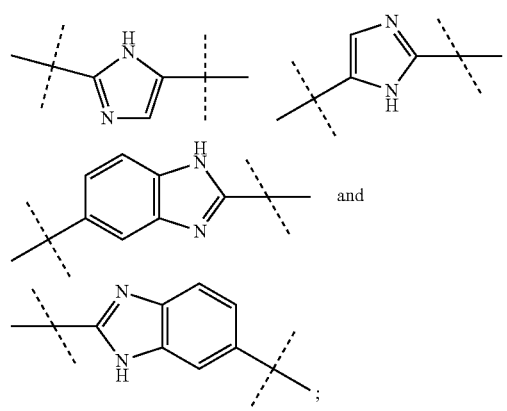

$Q^1$ and $Q^2$ are independently H or F;

or $Q^1$ and $Q^2$ together form heterocycloalkyl; and

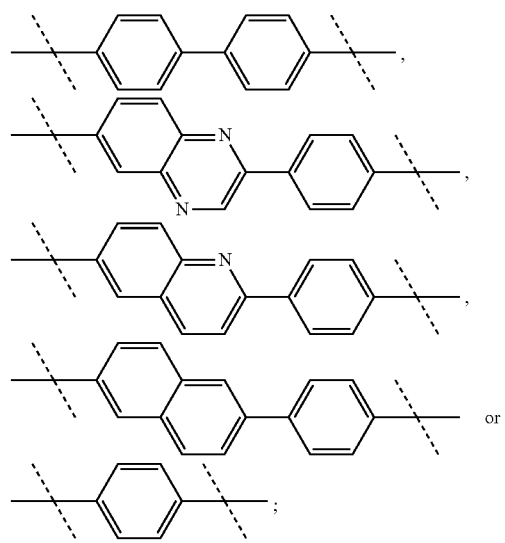

L is

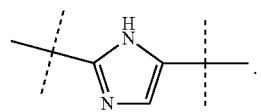

or a pharmaceutically acceptable salt thereof.

The application provides a compound of Formula I, wherein X is isopropyl.

The application provides a compound of Formula I, wherein R' is methyl.

The application provides a compound of Formula I, wherein R' is methyl and X is isopropyl.

The application provides a compound of Formula I or II, wherein R is methyl.

The application provides a compound of Formula I or II, wherein R is benzyl.

The application provides a compound of Formula II, wherein each R is methyl.

The application provides a compound of Formula I or II, wherein B is

.

The application provides a compound of Formula I or II, wherein D is

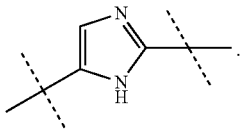

The application provides a compound of Formula I or II, wherein L is

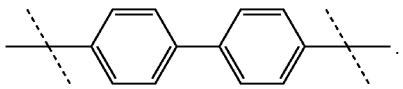

The application provides a compound of Formula I or II, wherein L is

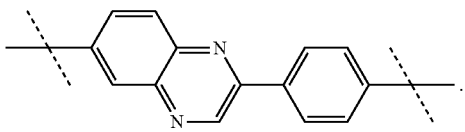

The application provides a compound of Formula I or II, wherein L is

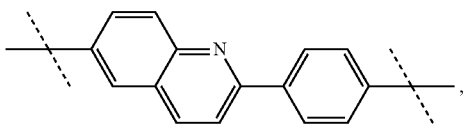

The application provides a compound of Formula I or II, wherein L is

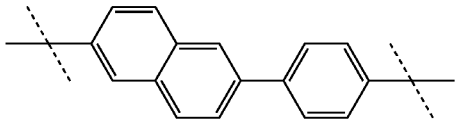

The application provides a compound selected from the group consisting of:

[(4S,7S)-4-(5-{4'-[2-((1S,9S)-9-[(Methoxycarbonyl)amino]-6,10-dioxo-octahydro-pyridazino[1,2-a][1,2]diazepin-1-yl)-3H-imidazol-4-yl]-biphenyl-4-yl}-1H-imidazol-2-yl)-6,10-dioxo-octahydro-pyridazino[1,2-a][1,2]diazepin-7-yl]-carbamic acid methyl ester;

{(4S,7S)-4-[5-(4-{2-[(S)-1-((S)-2-Methoxycarbonylamino-3-methyl-butyryl)-pyrrolidin-2-yl]-3H-imidazol-4-yl}-phenyl)-1H-benzoimidazol-2-yl]-6,10-dioxo-octahydro-pyridazino[1,2-a][1,2]diazepin-7-yl}-carbamic acid methyl ester;

{(4S,7S)-4-[5-(4'-{2-[(S)-1-((S)-2-Methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid benzyl ester;

((4S,7S)-4-{5-[4-(6-{2-[(S)-1-((S)-2-Methoxycarbonylamino-3-methyl-butyryl)-pyrrolidin-2-yl]-3H-imidazol-4-yl}-quinoxalin-2-yl)-phenyl]-1H-imidazol-2-yl}-6,10-dioxo-octahydro-pyridazino[1,2-a][1,2]diazepin-7-yl)-carbamic acid methyl ester;

{(4S,7S)-4-[5-(4'-{2-[(S)-4,4-Difluoro-1-((S)-2-methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester;

{(4S,7S)-4-[5-(4'-{2-[2-((S)-2-Methoxycarbonylamino-3-methyl-butyryl)-8-oxa-2-aza-spiro[4.5]dec-3-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester; and {(4S,7S)-4-[5-(4'-{2-[(S)-1-((S)-2-Methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester.

The application provides a method for treating a Hepatitis C Virus (HCV) infection comprising administering to a patient in need thereof a therapeutically effective amount of a compound of Formula I or II.

The application provides the above method, further comprising administering an immune system modulator or an antiviral agent that inhibits replication of HCV, or a combination thereof.

The application provides the above method, wherein the immune system modulator is an interferon or chemically derivatized interferon.

The application provides the above method, wherein the antiviral agent is selected from the group consisting of a HCV protease inhibitor, a HCV polymerase inhibitor, a HCV helicase inhibitor, a HCV primase inhibitor, a HCV fusion inhibitor, and a combination thereof.

The application provides a method for inhibiting replication of HCV in a cell comprising administering a compound of Formula I or II.

The application provides a composition comprising a compound of Formula I or II and a pharmaceutically acceptable excipient.

The application provides a method for treating a Hepatitis C Virus (HCV) infection comprising administering to a patient in need thereof a therapeutically effective amount of a compound of Formula I or II.

The application provides the above method, further comprising administering an immune system modulator or an antiviral agent that inhibits replication of HCV, or a combination thereof.

The application provides the above method, wherein the immune system modulator is an interferon or chemically derivatized interferon.

The application provides the above methods, wherein the antiviral agent is selected from the group consisting of a HCV protease inhibitor, a HCV polymerase inhibitor, a HCV helicase inhibitor, a HCV primase inhibitor, a HCV fusion inhibitor, and a combination thereof.

The application provides a method for inhibiting replication of HCV in a cell comprising administering a compound of Formula I or II.

The application provides a composition comprising a compound of Formula I or II and a pharmaceutically acceptable excipient.

The application provides the use of the compound of Formula I or II in the preparation of a medicament for the treatment of HCV.

The application provides any compound, composition, method or use as described herein.

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature.

If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of compounds according to generic Formulae I or II:

TABLE I

| # | Nomenclature | Structure |
|---|---|---|
| I-1 | [(4S,7S)-4-(5-{4'-[2-((1S,9S)-9-[(Methoxycarbonyl)amino]-6,10-dioxo-octahydro-pyridazino[1,2-a][1,2]diazepin-1-yl)-3H-imidazol-4-yl]-biphenyl-4-yl}-1H-imidazol-2-yl)-6,10-dioxo-octahydro-pyridazino[1,2-a][1,2]diazepin-7-yl]-carbamic acid methyl ester | 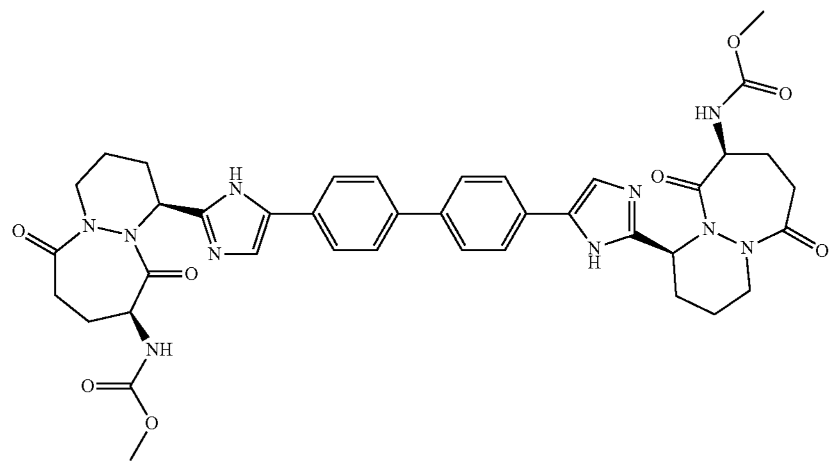 [SMILES: COC(=O)N[C@H]1CCC(=O)N2CCC[C@@H](c3ncc(-c4ccc(-c5ccc(-c6cnc([C@@H]7CCCN8C(=O)CC[C@H](NC(=O)OC)C(=O)N78)[nH]6)cc5)cc4)[nH]3)N2C1=O] |
| I-2 | {(4S,7S)-4-[5-(4-{2-[(S)-1-((S)-2-Methoxycarbonylamino-3-methyl-butyryl)-pyrrolidin-2-yl]-3H-imidazol-4-yl}-phenyl)-1H-benzoimidazol-2-yl]-6,10-dioxo-octahydro-pyridazino[1,2-a][1,2]diazepin-7-yl}-carbamic acid methyl ester | 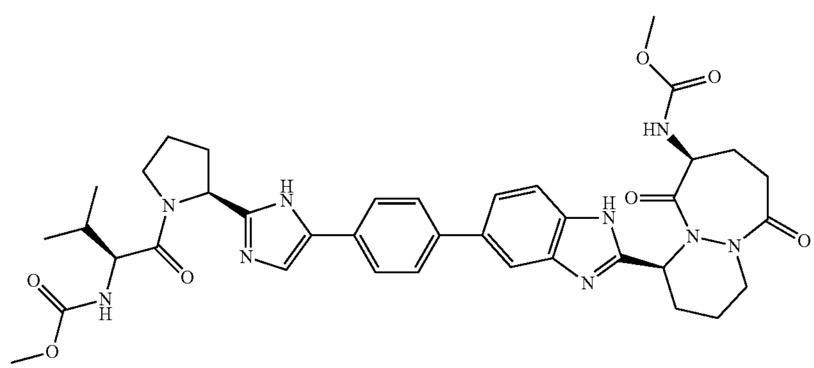 [SMILES: COC(=O)N[C@H]1CCC(=O)N2CCC[C@@H](c3nc4cc(-c5ccc(-c6cnc([C@@H]7CCCN7C(=O)[C@@H](NC(=O)OC)C(C)C)[nH]6)cc5)ccc4[nH]3)N2C1=O] |
| I-3 | {(4S,7S)-4-[5-(4'-{2-[(S)-1-((S)-2-Methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid benzyl ester | 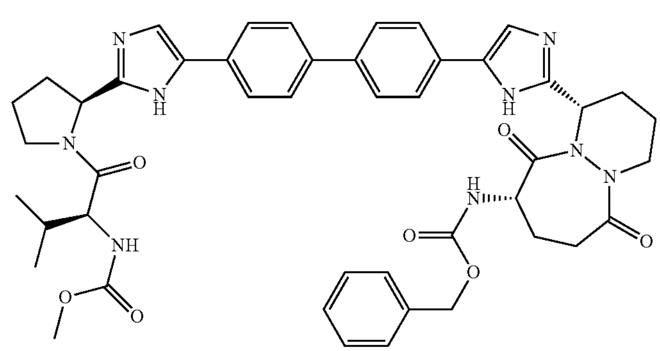 [SMILES: COC(=O)N[C@H](C(=O)N1CCC[C@H]1c1ncc(-c2ccc(-c3ccc(-c4cnc([C@@H]5CCCN6C(=O)CC[C@H](NC(=O)OCc7ccccc7)C(=O)N56)[nH]4)cc3)cc2)[nH]1)C(C)C] |

TABLE I-continued

| # | Nomenclature |
|---|---|
| I-4 | ((4S,7S)-4-{5-[4-(6-{2-[(S)-1-((S)-2-Methoxycarbonylamino-3-methyl-butyryl)-pyrrolidin-2-yl]-3H-imidazol-4-yl}-quinoxalin-2-yl)-phenyl]-1H-imidazol-2-yl}-6,10-dioxo-octahydro-pyridazino[1,2-a][1,2]diazepin-7-yl)-carbamic acid methyl ester |
| I-5 | {(4S,7S)-4-[5-(4'-{2-[(S)-4,4-Difluoro-1-((S)-2-methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester |
| I-6 | {(4S,7S)-4-[5-(4'-{2-[2-((S)-2-Methoxycarbonylamino-3-methyl-butyryl)-8-oxa-2-aza-spiro[4.5]dec-3-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester |
| I-7 | {(4S,7S)-4-[5-(4'-{2-[(S)-1-((S)-2-Methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester |

Synthesis
General Schemes

The following schemes depict general methods for obtaining compounds of Formulae I'-II'.

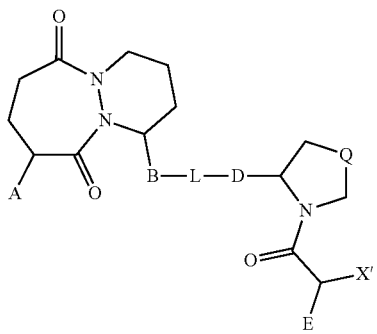

I'

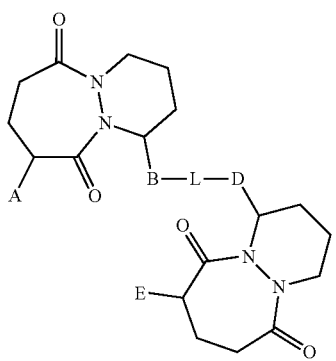

II'

The following schemes depict general methods for obtaining compounds of formula I.

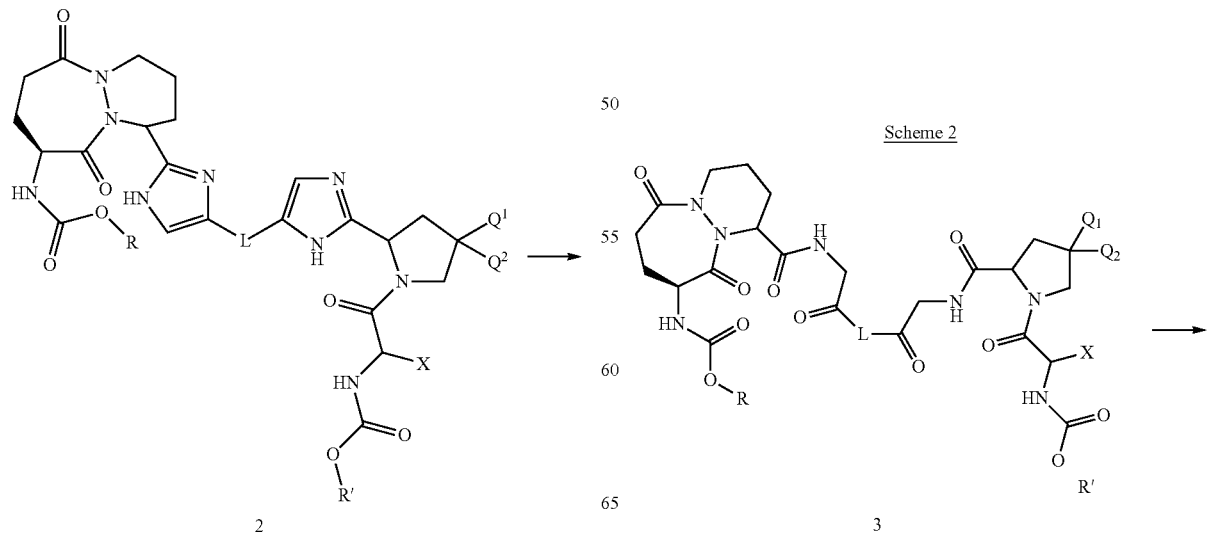

Compounds of formula I', wherein B and D are chloroimidazoles, and L are independently aryl or quinolinyl, naphthyl, quinazolinyl, or quinoxalinyl, 1 can be prepared from the corresponding imidazoles 2 using standard reaction conditions of chlorination of imidazole derivatives described for example, in Journal of Medicinal Chemistry (1986), 29(6), 1065-80; Journal of the Chemical Society, Perkin Transactions 1: Organic and Bio-Organic Chemistry (1972-1999) (1983) (4), 809-11; Eur. Pat. Appl. (1990) EP 365030 A1 19900425; Journal of Heterocyclic Chemistry (1994), 31(5), 1121-3; PCT Int. Appl. (2007), WO 2007070433. (Scheme 1)

Scheme 2

-continued

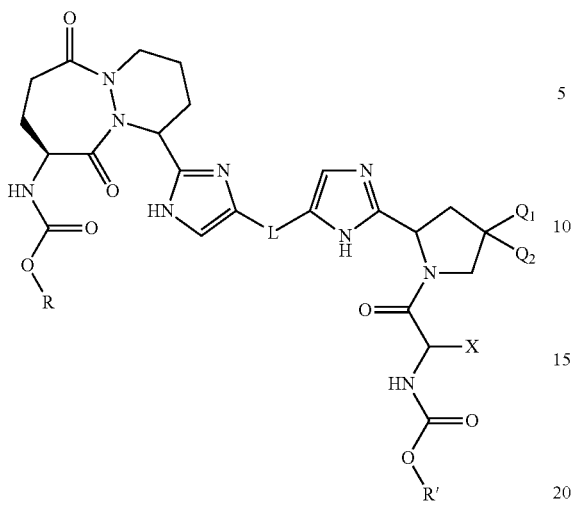

2

The imidazoles corresponding to 2 can be formed by the reaction of ammonium acetate on the keto-amide intermediates 3, as shown Scheme 2, using standard reaction conditions described, for example in, Journal of Organic Chemistry (1937), 2, 319-27; Synlett (2001), (2), 218-221.

Scheme 3

The keto-amide compounds of general formula 3, can be prepared from the corresponding carboxylic acid 5, and the amines of the formula 4, using standard methods of amide coupling.

(Scheme 3)

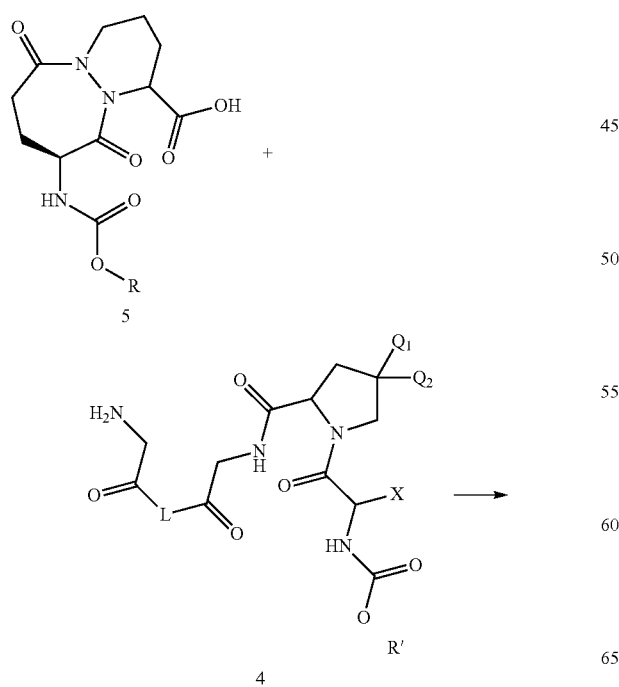

-continued

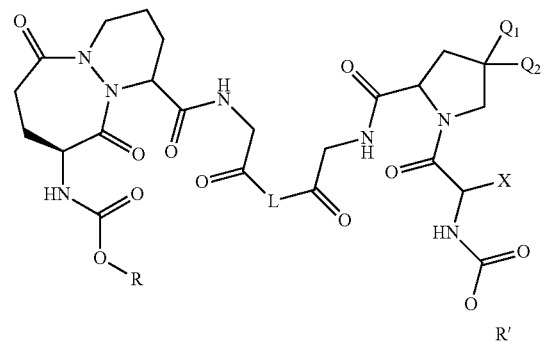

3

Scheme 4

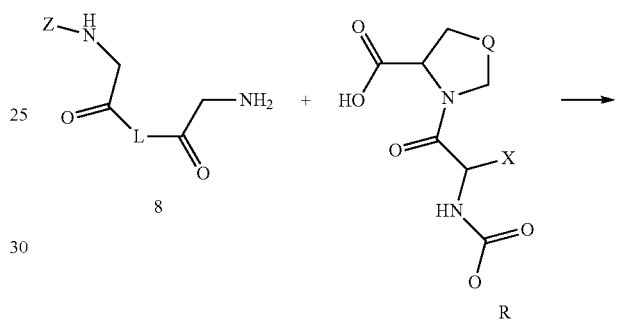

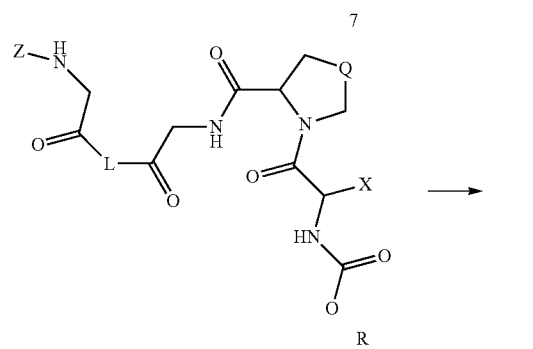

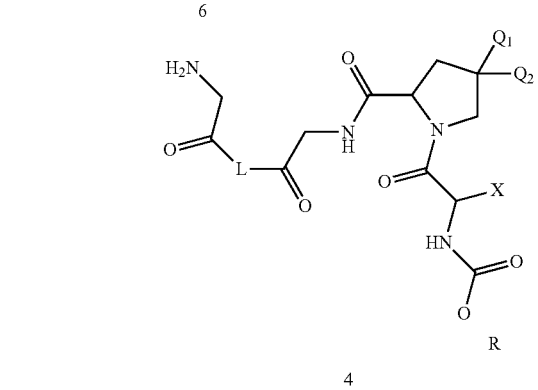

4

The amino-keto amides of formula 4 can be prepared from the corresponding bezyloxycarbonyl (Z) protected amine derivatives 6, via hydrogenation. The compounds of formula 6 can be assembled together via the coupling of carboxylic acid derivatives 7 and the differentially protected bis-amine derivatives 8 using standard methods of amide synthesis. (Scheme 4)

Scheme 5

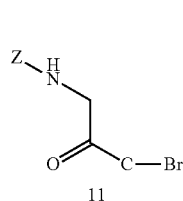

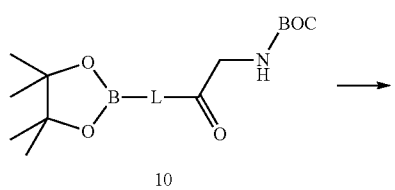

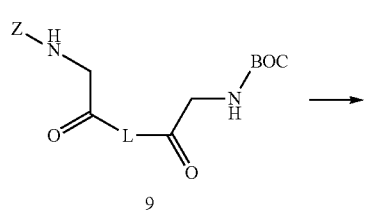

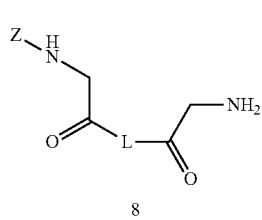

Compounds of formula 8 may be prepared from a differentially protected bis-amine derivatives 9 with a selective removal of BOC protecting group using standard methods of deprotection of a BOC group. Compounds of formula 9 may in turn be prepared in various methods including, for example the one shown in Scheme 5. In this method, an aryl bromide derivative 11 may be coupled with a boronate ester derivative 10 under Pd⁰ coupling conditions to provide compounds of formula 9. The boronate esters 10 and the bromo aryl derivatives 9 can be prepared starting from corresponding bromoaryl acetophenones via reported methods. See for example, (BMS patents).

The compounds of formula 5 are can be prepared starting from 13 (Attwood, M. R et al, *Journal of the Chemical Society, Perkin Transactions 1: Organic and Bio-Organic Chemistry* (1972-1999) 1986, 1011-19) via its conversion to the derivative 12, which can be transformed into compounds of formula 5 via standard carbamate forming reactions. (Scheme 6)

Scheme 6

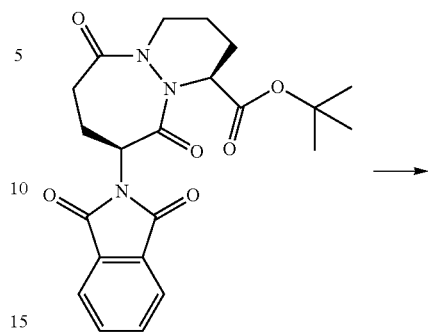

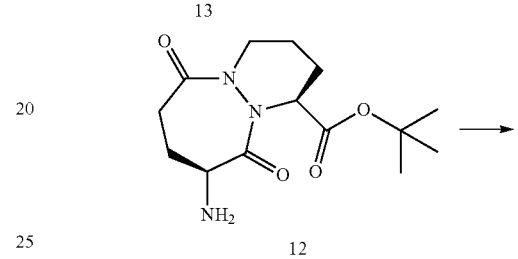

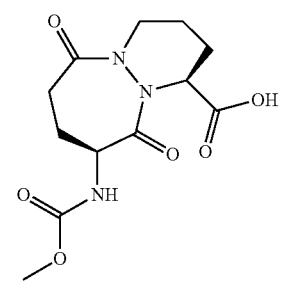

Compounds of formula 7 can be prepared starting from commercially available proline derivatives such as H-Pro-OMe or 3,3-difluoro-Pro-OH and their coupling with various amino acid derivatives using standard methods of amide coupling.

Compounds of formula I', wherein E is a benzimidazole moiety, may be prepared following the reaction sequence shown (Scheme 7).

Scheme 7

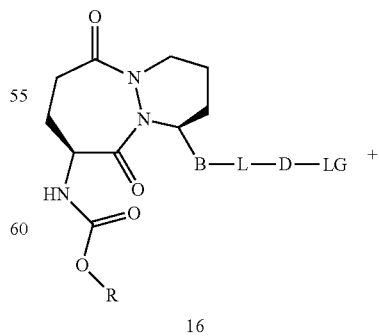

LG (leaving group) = OSO₂CF₃ or Cl/Br/I

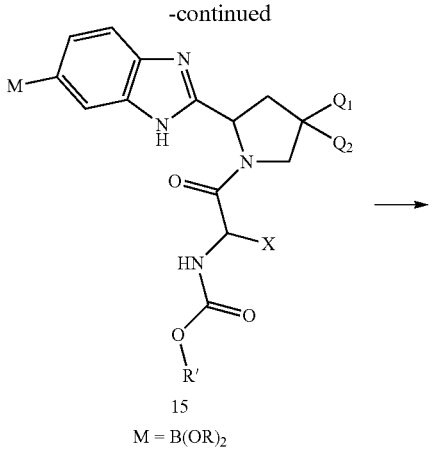

15
M = B(OR)₂

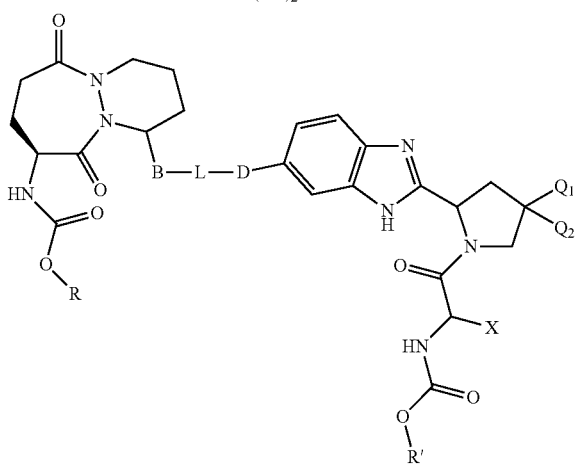

14

Compounds of formula 16 can be coupled with compounds of formula 15 via standard Pd⁰-coupling methods to yield target compounds of formula 14 or Ib. Compounds of formula 15 can be readily prepared from the sequence of reactions shown in Scheme 8.

Dosage and Administration:

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Indications and Method of Treatment
Indications

The compounds of the invention and their isomeric forms and pharmaceutically acceptable salts thereof are useful in treating and preventing HCV infection.

The application provides a method for treating a Hepatitis C Virus (HCV) infection comprising administering to a patient in need thereof a therapeutically effective amount of a compound of Formula I or II.

The application provides a method for inhibiting replication of HCV in a cell comprising administering a compound of Formula I or II.

Combination Therapy

The compounds of the invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention include, without limitation, all classes of HCV antivirals.

For combination therapies, mechanistic classes of agents that can be useful when combined with the compounds of the invention include, for example, nucleoside and non-nucleoside inhibitors of the HCV polymerase, protease inhibitors, helicase inhibitors, NS4B inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-9005 18), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor), VX-500, VX-8 13, PHX-1766, PHX2054, IDX-136, IDX-3 16, ABT-450 EP-0 13420 (and congeners) and VBY-376; the Nucleosidic HCV polymerase (replicase) inhibitors useful in the invention include, but are not limited to, R7128, PSI-785 1, IDX-184, IDX-102, R1479, UNX-08 189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nucleosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, compounds of the invention can be used in combination with cyclophyllin and immunophyllin antagonists (e.g., without limitation, DEBIO compounds, NM-811 as well as cyclosporine and its derivatives), kinase inhibitors, inhibitors of heat shock proteins (e.g., HSP90 and HSP70), other immunomodulatory agents that can include, without limitation, interferons (-alpha, -beta, -omega, -gamma, -lambda or synthetic) such as Intron A, Roferon-A, Canferon-A300, Advaferon, Infergen, Humoferon, Sumiferon MP, Alfaferone, IFN-β, Feron and the like; polyethylene glycol derivatized (pegylated) interferon compounds, such as PEG interferon-α-2a (Pegasys), PEG interferon-α-2b (PEGIntron), pegylated IFN-α-con1 and the like; long acting formulations and derivatizations of interferon compounds such as the albumin-fused interferon, Albuferon, Locteron, and the like; interferons with various types of controlled delivery systems (e.g., ITCA-638, omega-interferon delivered by the DUROS subcutaneous delivery system); compounds that stimulate the synthesis of interferon in cells, such as resiquimod and the like; interleukins; compounds that enhance the development of e 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV ElE2MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL, REMICADE, and HUMIRA.

In addition, compounds of the invention can be used in combination with antiprotozoans and other antivirals thought to be effective in the treatment of HCV infection such as, without limitation, the prodrug nitazoxanide. Nitazoxanide can be used as an agent in combination with the compounds disclosed in this invention as well as in combination with other agents useful in treating HCV infection such as peginterferon α-2a and ribavirin.

Compounds of the invention can also be used with alternative forms of interferons and pegylated interferons, ribavirin or its analogs (e.g., tarabavarin, levoviron), microRNA, small interfering RNA compounds (e.g., SIRPLEX-140-N and the like), nucleotide or nucleoside analogs, immunoglobulins, hepatoprotectants, anti-inflammatory agents and other inhibitors of NS5A. Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative HCV inhibitor compounds include those disclosed in the following publications: U.S. Pat. Nos. 5,807,876; 6,498,178; 6,344, 465; and 6,054,472; PCT Patent Application Publication Nos. WO97/40028; W0984038 1; WO00/56331, WO02/04425; WO03/007945; WO03/010141; WO03/000254; WO01/ 32153; WO00/06529; WO00/8231; WO00/0573; WO00/ 3708; WO01/85172; WO03/037893; WO03/037894; WO03/ 037895; WO02/00851; WO02/00846; WO99/01582; WO00/ 09543; WO02/18369; WO98/17679, WO00/056331; WO98/ 22496; WO99/07734; WO05/073216, WO05/073195 and WO08/021927.

Additionally, combinations of, for example, ribavirin and interferon, may be administered as multiple combination therapy with at least one of the compounds of the invention. The present invention is not limited to the aforementioned classes or compounds and contemplates known and new compounds and combinations of biologically active agents. It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the judgment of the one skilled in the art administering or supervising the administration of the combination therapy.

The application provides a method for treating a Hepatitis C Virus (HCV) infection comprising administering to a patient in need thereof a therapeutically effective amount of a compound of Formula I or II.

The application provides the above method, further comprising administering an immune system modulator or an antiviral agent that inhibits replication of HCV, or a combination thereof.

The application provides the above method, wherein the immune system modulator is an interferon or chemically derivatized interferon.

The application provides the above methods, wherein the antiviral agent is selected from the group consisting of a HCV protease inhibitor, a HCV polymerase inhibitor, a HCV helicase inhibitor, a HCV primase inhibitor, a HCV fusion inhibitor, and a combination thereof.

EXAMPLES

Abbreviations

Commonly used abbreviations include: acetyl (Ac), azo-bis-isobutyrylnitrile (AIBN), atmospheres (Atm), 9-borabi-cyclo[3.3.1]nonane (9-BBN or BBN), 2,2'-bis(diphenylphos-phino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propyl-ethylamine (DIPEA), N,N-dimethyl acetamide (DMA), 4-N, N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether ($Et_2O$), ethyl isopropyl ether (EtOiPr), 0-(7-azabenzotriaz-ole-1-yl)-N, N,N'N'-tetramethyluronium hexafluorophosphate acetic acid (HATU), acetic acid (HOAc), 1-N-hydroxy-benzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpho line (NMM), N-methylpyrrolidone (NMP), pyridinium chlorochromate (PCC), Dichloro-((bis-diphenylphosphino)ferrocenyl) palladium(II) (Pd(dppf)$Cl_2$), palladium(II) acetate (Pd(OAc)$_2$), tris(dibenzylideneac-etone)dipalladium(0) ($Pd_2(dba)_3$), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-BuMe$_2$Si (TBDMS), tetra-n-butylammonium fluoride (TBAF), triethylamine (TEA or Et$_3$N), 2,2,6,6-tetramethylpiperidine 1-oxyl (TEMPO), triflate or CF$_3$SO$_2$— (TO, trifluoroacetic acid (TFA), 1,1'-bis-2,2,6,6-tetramethylheptane-2,6-dione (TMHD), 0-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

General Conditions

Compounds of the invention can be made by a variety of methods depicted in the illustrative synthetic reactions described below in the Examples section.

The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991, Volumes 1-15; Rodd's *Chemistry of Carbon Compounds*, Elsevier Science Publishers, 1989, Volumes 1-5 and Supplementals; and *Organic Reactions*, Wiley & Sons: New York, 1991, Volumes 1-40. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Various substituents on the compounds of the invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "*Protective Groups in Organic Synthesis*" by Green et al., John Wiley and Sons, 1999. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Preparative Examples

Example 1

[(4S,7S)-4-(5-{4'-[2-(1S,9S)-9-[(Methoxycarbonyl)amino]-6,10-dioxo-octahydro-pyridazino[1,2-a][1,2]diazepin-1-yl]-3H-imidazol-4-yl]-biphenyl-4-yl}-1H-imidazol-2-yl)-6,10-dioxo-octahydro-pyridazino[1,2-a][1,2]diazepin-7-yl]-carbamic acid methyl ester trifluoroacetic acid (1:2)

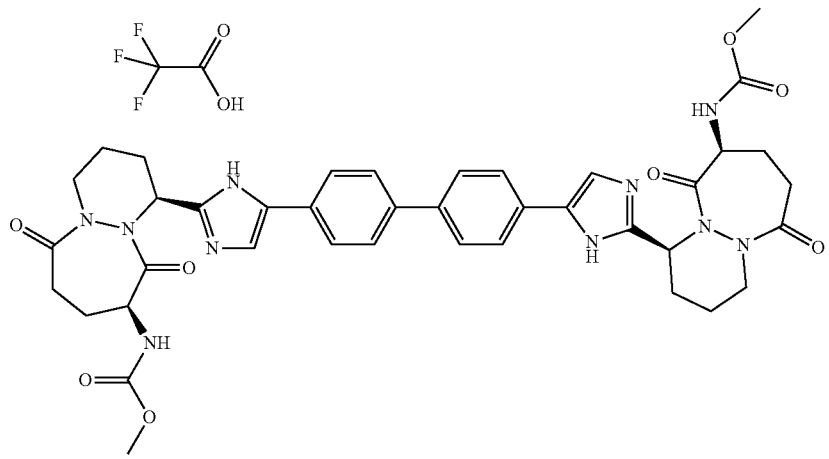

To a solution of (1S,9S)-tert-butyl 9-(1,3-dioxoisoindolin-2-yl)-6,10-dioxooctahydro-1H-pyridazino[1,2-a][1,2]diazepine-1-carboxylate (2.00 g, 4.68 mmol) in ethanol (10 mL) was added hydrazine (180 mg, 5.61 mmol). The reaction was stirred at room temperature for 3 h. The ethanol and excess hydrazine were concentrated in vacuo and the residue co-evaporated with ethanol to afford, (1S,9S)-tert-butyl 9-amino-6,10-dioxooctahydro-1H-pyridazino[1,2-a][1,2]diazepine-1-carboxylate as a white powder, (1.63 g, 100%): ESI-LRMS m/e calcd for $C_{14}H_{23}N_3O_4[M^+]$ 297. found 298 $[M+H^+]$.

To an ice-cooled solution of (1S,9S)-tert-butyl 9-amino-6,10-dioxooctahydro-1H-pyridazino[1,2-a][1,2]diazepine-1-carboxylate (1.50 g, 5.04 mmol) in DMF (15 mL) was added sodium carbonate (642 mg, 6.05 mmol) followed by methyl chloroformate (524 mg, 5.55 mmol). After the addition was complete the ice bath was removed and the reaction stirred at room temperature for 2 h. The reaction mixture was diluted with ethyl acetate and washed with water 2N hydrochloric acid, a saturated sodium chloride solution and dried over magnesium sulfate, filtered and concentrated to afford, (1S,9S)-tert-butyl 9-(methoxycarbonylamino)-6,10-dioxooctahydro-1H-pyridazino[1,2-a][1,2]diazepine-1-carboxylate as a white solid, (1.28 g, 71%): ESI-LRMS m/e calcd for $C_{16}H_{25}N_3O_6[M^+]$ 355. found 356 $[M+H^+]$.

To a solution of (1S,9S)-tert-butyl 9-(methoxycarbonylamino)-6,10-dioxooctahydro-1H-pyridazino[1,2-a][1,2]diazepine-1-carboxylate (1.25 g, 3.52 mmol) dissolved into methylene chloride (10 mL) was added trifluoroacetic acid (10 mL). The reaction was stirred at room temperature for 1 h and concentrated in vacuo. Toluene (5 mL) was added and the reaction concentrated in vacuo to afford (1S,9S)-9-(methoxycarbonylamino)-6,10-dioxooctahydro-1H-pyridazino[1,2-a][1,2]diazepine-1-carboxylic acid as a white solid, (587 mg, 68%): ESI-LRMS m/e calcd for $C_{12}H_{17}N_3O_6[M^+]$ 299. found 300 $[M+H^+]$.

DMF (3 ml) was treated with N,N'-diisopropylethylamine (270 mg, 380 µl, 2.09 mmol, Eq: 6.00). The reaction mixture was stirred for 16 h at 23° C. The reaction mixture after aqueous acidic work-up to afford, dimethyl (4S,4'S,7S,7'S)-4,4'-(2,2'-(biphenyl-4,4'-diyl)bis(2-oxoethane-2,1-diyl))bis(azanediyl)bis(oxomethylene)bis(6,10-dioxooctahydro-1H-pyridazino[1,2-a][1,2]diazepine-7,4-diyl)dicarbamate, as a light red gum. (345.8 mg, 77.6%): ESI-LRMS m/e calcd for $C_{40}H_{46}N_8O_{12}[M^+]$ 830. found 831 $[M+H^+]$.

A solution of dimethyl (4S,4'S,7S,7'S)-4,4'-(2,2'-(biphenyl-4,4'-diyl)bis(2-oxoethane-2,1-diyl))bis(azanediyl)bis(oxomethylene)bis(6,10-dioxooctahydro-1H-pyridazino[1,2-a][1,2]diazepine-7,4-diyl)dicarbamate (345 mg, 270 µmol, Eq: 1.00) and ammonium acetate (208 mg, 2.7 mmol, Eq: 10.00) in a mixture of solvents, Xylene (2 ml) and Dioxane (4 ml) was heated in a sealed at 140° C. for 4 h. The reaction mixture was cooled to 23° C., and solids were separated. The solution was concentrated in vacuo, to yield 209.7 mg crude product as light red gum. This material was purified on the CombiFlash machine, using 25 g silica gel cartridge, methylene chloride, 10%-methanol-methylene chloride with a gradient of 0-70%. The product was eluted with 5% methanol-methylene chloride. Yield—30.6 mg as light red powder. This material further purified on a reverse phase HPLC, using 0.1% TFA water—0.1% acetonitrile system, to yield 10 mg as TFA salt, white fluffy solid. ESI-LRMS m/e calcd $C_{40}H_{44}N_{10}O_8 [M^+]$ 792. found 792, $[M+H^+]$, $^1H$ NMR (400 MHz, DMSO-$d_6$) d 7.78-8.00 (m, 8H), 7.63 (d, J=7.78 Hz, 2H), 5.96 (br, 2H), 4.54 (br, 4H), 3.68 (s, 6H), 3.25 (br, 2H), 3.06 (br, 2H), 2.36 (m, 6H), 2.24 (dd, J=6.65, 12.42 Hz, 2H), 1.94-2.18 (m, 6H), 1.80 (br. s., 2H).

Example 2

{(4S,7S)-4-[5-(4-{2-[(S)-1-((S)-2-Methoxycarbonylamino-3-methyl-butyryl)-pyrrolidin-2-yl]-3H-imidazol-4-yl}-phenyl)-1H-benzoimidazol-2-yl]-6,10-dioxo-octahydro-pyridazino[1,2-a][1,2]diazepin-7-yl}-carbamic acid methyl ester dihydrochloride

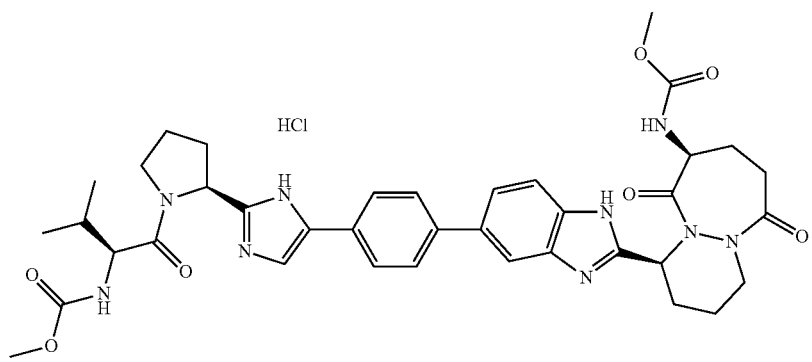 [SMILES: COC(=O)N[C@H]1CCC(=O)N2CCC[C@@H](c3nc4cc(-c5ccc(-c6cnc([C@@H]7CCCN7C(=O)[C@@H](NC(=O)OC)C(C)C)[nH]6)cc5)ccc4[nH]3)N2C1=O ; Cl]

A suspension of (1S,9S)-9-(methoxycarbonylamino)-6,10-dioxooctahydro-1H-pyridazino[1,2-a][1,2]diazepine-1-carboxylic acid (219 mg, 732 µmol, Eq: 2.10), 1,1'-(biphenyl-4,4'-diyl)bis(2-aminoethanone) dihydrochloride (119 mg, 349 µmol, Eq: 1.00) (ref. Bachand, C., et al WO 2008021927), and HATU (285 mg, 750 µmol, Eq: 2.15) in A solution of (1S,9S)-9-(methoxycarbonylamino)-6,10-dioxooctahydro-1H-pyridazino[1,2-a][1,2]diazepine-1-carboxylic acid (184.7 mg, 605 µmol), 4-bromobenzene-1,2-diamine (124 mg, 665 µmol), HATU (230 mg, 605 µmol, Eq: 1.00) in DMF (3 ml) was treated with N,N'-diisopropylethylamine (235 mg, 317 µl, 1.81 mmol, Eq: 3.00). The solution was stirred at 23° C. for 16 h. The reaction mixture was diluted with ethyl acetate, washed with water, brine and dried over MgSO$_4$. The organic layer was concentrated to yield 317.3 mg a 1:1 mixture of [(4S,7S)-4-(2-Amino-4-bromo-phenylcarbamoyl)-6,10-dioxo-octahydro-pyridazino[1,2-a][1,2]diazepin-7-yl]-carbamic acid methyl ester and [(4S,7S)-4-(2-Amino-5-bromo-phenylcarbamoyl)-6,10-dioxo-octahydro-pyridazino[1,2a][1,2]diazepin-7-yl]-carbamic acid methyl ester, as a light brown solid. This mixture was used as such for the next step. A solution of the mixture (317 mg, 508 µmol) in acetic acid (3.12 g, 3 mL, 52.0 mmol) was heated for 1 hr at 90° C. The reaction mixture was cooled to 23° C., and concentrated in vacuo. The residue was dissolved in ethyl acetate (30 mL) washed with sat. NaHCO3, brine and dried (MgSO$_4$). The organic layer was concentrated to yield [(4S,7S)-4-(5-bromo-1H-benzoimidazol-2-yl)-6,10-dioxo-octahydro-pyridazino[1,2-a][1,2]diazepin-7-yl]-carbamic acid methyl ester as light brown powder (191.3 mg, 79.5%). ESI-LRMS m/e calcd for C$_{18}$H$_{20}$BrN$_5$O$_4$ [M$^+$] 449. found 450 [M+H$^1$].

A solution of methyl (4S,7S)-4-(5-bromo-1H-benzo[d]imidazol-2-yl)-6,10-dioxooctahydro-1H-pyridazino[1,2-a][1,2]diazepin-7-ylcarbamate (190 mg, 405 µmol), methyl (S)-3-methyl-1-oxo-1-((S)-2-(4-(4-(4,4,5,5-tetramethyl-1,3,2-dioxaborolan-2-yl)phenyl)-1H-imidazol-2-yl)pyrrolidin-1-yl)butan-2-ylcarbamate (223 mg, 405 µmol), in 1,2-Dimethoxyethane (6 ml) was treated with sodium bicarbonate (103 mg, 1.22 mmol). The mixture was de-oxygenated by bubbling argon for 15 min. Then, [1,1'-bis(diphenylphosphino)ferrocene]-dichloropalladium (II) (44.9 mg, 60.8 µmol) was added and the reaction vessel was capped and lowered into a pre-heated oil bath kept at 90° C., and heated for 14 h. The reaction mixture was filtered and concentrated. The residue was taken up in 10% methanol-methylene chloride and washed with water and brine, and dried over MgSO$_4$. The organic layer, upon concentration yielded crude product as brown gum. The crude product was purified on an ISCO Commander machine, using 0-100%-10% methanol-methylene chloridemethylene chloride gradient over 25 min. The product was eluted around 70%-10% methanol-methylene chloridemethylene chloride. {(4S,7S)-4-[5-(4-{2-[(S)-1-((S)-2-Methoxycarbonylamino-3-methyl-butyryl)-pyrrolidin-2-yl]-3H-imidazol-4-yl}-phenyl)-1H-benzoimidazol-2-yl]-6,10-dioxo-octahydro-pyridazino[1,2-a][1,2]diazepin-7-yl}-carbamic acid methyl ester was isolated as sticky brown solid—16.5 mg. This material was dissolved in ethanol (3 mL) and treated with 4N HCl in dioxane (1 mL). The solution was stirred for 10 min. Then, it was concentrated and additional 3 mL of ethanol was added and concentrated again, to yield {(4S,7S)-4-[5-(4-{2-[(S)-1-((S)-2-Methoxycarbonylamino-3-methyl-butyryl)-pyrrolidin-2-yl]-3H-imidazol-4-yl}-phenyl)-1H-benzoimidazol-2-yl]-6,10-dioxo-octahydro-pyridazino[1,2-a][1,2]diazepin-7-yl}-carbamic acid methyl ester dihydrochloride as brown powder (16.5 mg, 4.8%). ESI-LRMS m/e calcd for C$_{38}$H$_{45}$N$_5$O$_7$[M$^+$] 739. found 740 [M+H$^1$], $^1$H NMR (400 MHz, DMSO-d$_6$) δ 8.14 (s, 1H), 7.82-7.98 (m, 5H), 7.65 (br. s. 2H), 7.49-7.59 (m, 2H), 7.33 (d, J=8.03 Hz, 1H), 6.04 (br. s., 1H), 5.11-5.20 (m, 1H), 4.43 (d, J=12.30 Hz, 2H), 4.08-4.18 (m, 2H), 3.89 (m, 2H), 3.69 (dd, J=5.02, 14.56 Hz, 3H), 3.55 (d, J=10.54 Hz, 3H), 3.20 (m, 1H), 2.95 (m, 1H), 2.40 (d, J=6.53 Hz, 1H), 1.82-2.31 (m, 10H), 1.73 (br. s. 1H), 0.71-0.97 (m, 6H).

Example 3

{(4S,7S)-4-[5-(4'-{2-[(S)-1-((S)-2-Methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid benzyl ester

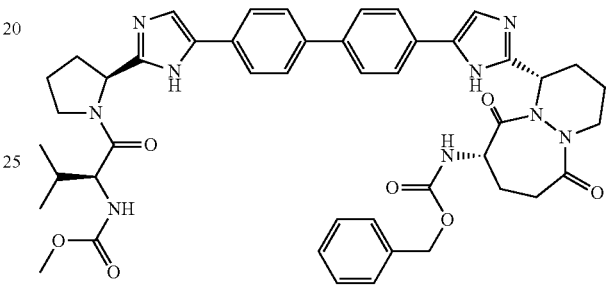

In a 10 mL seal tube, methyl (S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-ylcarbamate (55 mg, 111 µmol) (Intermediate 1), benzyl (4S,7S)-4-(5-(4-bromophenyl)-1H-imidazol-2-yl)-6,10-dioxooctahydro-1H-pyridazino[1,2-a][1,2]diazepin-7-ylcarbamate (61.2 mg, 111 µmol) (Intermediate 6) and sodium bicarbonate (sat. solution, 600 µl, excess) were combined with tert-butanol (3.00 ml) to give a light brown suspension and degassed for 5 min. PdCl$_2$ (DPPF) (8.11 mg, 11.1 µmol) was added and flushed with nitrogen. It was sealed heating at 90° C. for 4 hr then diluted with EtOAc (10 ml), filtered and concentrated. The crude was purified on a silica gel column (CH$_2$Cl$_2$, 2%, 3%, 5%, 8% MeOH/CH$_2$Cl$_2$) to afford {(4S,7S)-4-[5-(4'-{2-[(S)-1-((S)-2-Methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid benzyl ester as a light yellow solid (30 mg, 30.6%). ESI-LRMS m/e calcd for C$_{46}$H$_{51}$N$_9$O$_7$, [M$^+$] 841. found 842 [M+H]. $^1$H NMR (DMSO-d$_6$) δ: 12.23 (br. s., 1H), 11.66-11.89 (m, 1H), 7.72-7.85 (m, 5H), 7.58-7.92 (m, 4H), 7.48-7.55 (m, 1H), 7.34-7.43 (m, 3H), 7.22-7.35 (m, 1H), 7.19-7.45 (m, 3H), 5.81 (br. s., 1H), 5.77-5.86 (m, 1H), 5.01-5.13 (m, 3H), 4.92-5.21 (m, 2H), 4.47 (d, J=11.5 Hz, 1H), 4.33-4.59 (m, 1H), 4.00-4.13 (m, 1H), 3.95-4.13 (m, 1H), 3.72-3.86 (m, 1H), 3.81 (br. s., 1H), 3.54 (s, 3H), 3.45-3.64 (m, 2H), 2.82-3.00 (m, 1H), 2.79-2.96 (m, 1H), 2.08-2.35 (m, 2H), 1.76-2.05 (m, 3H), 1.50-1.67 (m, 1H), 0.80-0.95 (m, 6H).

Example 4

(4S,7S)-4-{5-[4-(6-{2-[(S)-1-((S)-2-Methoxycarbonylamino-3-methyl-butyryl)-pyrrolidin-2-yl]-3H-imidazol-4-yl}-quinoxalin-2-yl)-phenyl]-1H-imidazol-2-yl}-6,10-dioxo-octahydro-pyridazino[1,2-a][1,2]diazepin-7-yl)-carbamic acid methyl ester

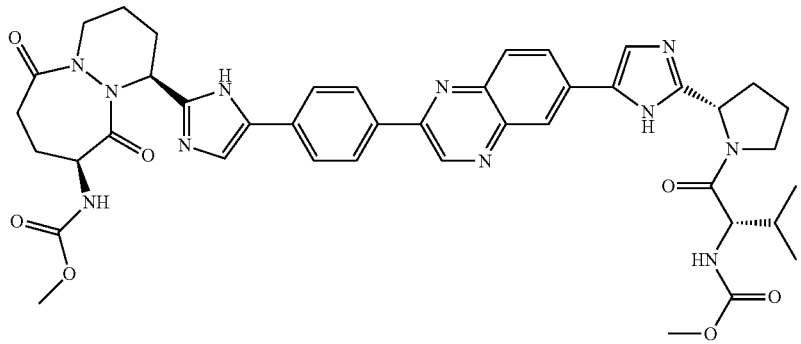 [SMILES: COC(=O)N[C@H]1CCC(=O)N2CCC[C@@H](c3ncc(-c4ccc(-c5cnc6cc(-c7cnc([C@@H]8CCCN8C(=O)[C@@H](NC(=O)OC)C(C)C)[nH]7)ccc6n5)cc4)[nH]3)N2C1=O]
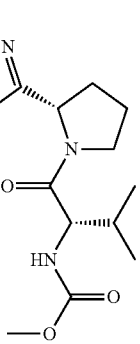

In a 10 mL pear-shaped flask, (S)-2-(methoxycarbonylamino)-3-methylbutanoic acid (8.35 mg, 47.7 µmol) was combined with DMF (1 ml) (1 ml) to give a colorless solution. HATU (14.5 mg, 38.1 µmol) was added and stirred for 10 min. methyl (4S,7S)-6,10-dioxo-4-(5-(4-(6-(2-((S)-pyrrolidin-2-yl)-1H-imidazol-5-yl)quinoxalin-2-yl)phenyl)-1H-imidazol-2-yl)octahydro-1H-pyridazino[1,2-a][1,2]diazepin-7-ylcarbamate (21 mg, 31.8 µmol) in 2 ml of DMF and DIPEA (20.5 mg, 27.8 µl, 159 µmol) were added and stirred at room temperature for 1 hr. It was diluted with brine and H₂O (10 ml each) and the precipitate was filtered, washed with H₂O and hexane, dried on high vacuum at 46° C. to afford ((4S,7S)-4-{5-[4-(6-{2-[(S)-1-((S)-2-Methoxycarbonylamino-3-methyl-butyryl)-pyrrolidin-2-yl]-3H-imidazol-4-yl}-quinoxalin-2-yl)-phenyl]-1H-imidazol-2-yl}-6,10-dioxo-octahydro-pyridazino[1,2-a][1,2]diazepin-7-yl)-carbamic acid methyl ester as a light brownish solid (15 mg, 53.1%). ESI-LRMS m/e calcd for $C_{42}H_{47}N_{11}O_7$, $[M^+]$ 817. found 818 [M+H]. $^1$H NMR (DMSO-d₆) δ: 12.34 (br. s., 1H), 12.02 (br. s., 1H), 9.29-9.68 (m, 1H), 8.21-8.52 (m, 4H), 7.71-8.11 (m, 5H), 7.15-7.60 (m, 2H), 5.83 (br. s., 1H), 5.12 (br. s., 1H), 4.46 (br. s., 3H), 4.09 (br. s., 1H), 3.85 (br. s., 3H), 3.56 (d, J=7.5 Hz, 6H), 2.90 (br. s., 3H), 1.56-2.39 (m, 8H), 0.76-1.06 (m, 6H).

Example 5

{(4S,7S)-4-[5-(4'-{2-[(S)-4,4-Difluoro-1-((S)-2-methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester

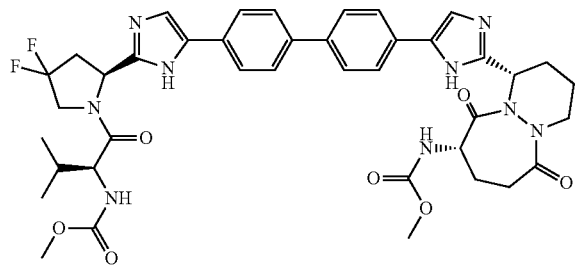 [SMILES: COC(=O)N[C@H]1CCC(=O)N2CCC[C@@H](c3ncc(-c4ccc(-c5ccc(-c6cnc([C@@H]7CC(F)(F)CN7C(=O)[C@@H](NC(=O)OC)C(C)C)[nH]6)cc5)cc4)[nH]3)N2C1=O]

In a 10 mL seal tube, methyl (S)-1-((S)-4,4-difluoro-2-(5-(4-(4,4,5,5-tetramethyl-1,3,2-dioxaborolan-2-yl)phenyl)-1H-imidazol-2-yl)pyrrolidin-1-yl)-3-methyl-1-oxobutan-2-ylcarbamate (52 mg, 97.7 µmol), methyl (4S,7S)-4-(5-(4-bromophenyl)-1H-imidazol-2-yl)-6,10-dioxooctahydro-1H-pyridazino[1,2-a][1,2]diazepin-7-ylcarbamate (46.5 mg, 97.7 µmol) and sodium bicarbonate (sat. solution, 400 µl, excess) were combined with tert-butanol (2.00 ml) to give a light brown suspension and degassed for 5 min. PdCl₂(DPPF) (7.15 mg, 9.77 µmol) was added and flushed with nitrogen. It was sealed heating at 90° C. for 4 hr, diluted with EtOAc (10 ml), filtered and concentrated in vacuo. The crude mixture was purified on a silica gel column (CH₂Cl₂, 2%, 3%, 5%, 8% MeOH/CH₂Cl₂) to afford {(4S,7S)-4-[5-(4'-{2-[(S)-4,4-Difluoro-1-((S)-2-methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester as a light yellow solid (26 mg, 31.5%). ESI-LRMS m/e calcd for $C_{40}H_{45}F_2N_9O_7$, $[M^+]$ 801. found 802 [M+H]. $^1$H NMR (DMSO-d₆) δ: 12.23 (br. s., 1H), 11.98 (br. s., 1H), 7.72-7.84 (m, 4H), 7.62-7.72 (m, 5H), 7.57 (d, J=1.8 Hz, 1H), 7.50 (d, J=8.0 Hz, 2H), 5.81 (br. s., 1H), 5.30 (t, J=7.5 Hz, 1H), 4.39-4.55 (m, 3H), 3.94 (t, J=8.2 Hz, 1H), 3.56 (s, 4H), 3.55 (br. s., 3H), 2.84-2.95 (m, 1H), 2.18-2.35 (m, 3H), 2.12 (dd, J=13.1, 6.5 Hz, 1H), 1.86-2.03 (m, 4H), 1.64 (d, J=13.3 Hz, 1H), 1.09-1.26 (m, 1H), 0.92 (d, J=6.5 Hz, 1H), 0.85 (d, J=6.5 Hz, 6H).

Example 6

{(4S,7S)-4-[5-(4'-{2-[2-((S)-2-Methoxycarbonylamino-3-methyl-butyryl)-8-oxa-2-aza-spiro[4.5]dec-3-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester

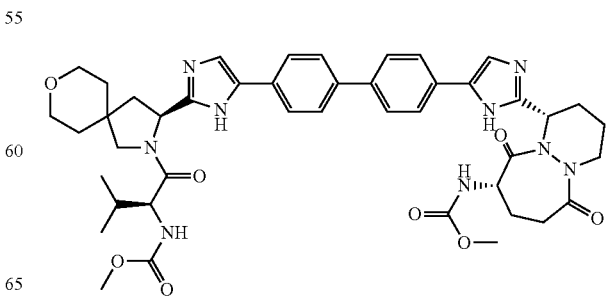

In a 10 mL seal tube, methyl (2S)-3-methyl-1-oxo-1-(3-(5-(4-(4,4,5,5-tetramethyl-1,3,2-dioxaborolan-2-yl)phenyl)-1H-imidazol-2-yl)-8-oxa-2-azaspiro[4.5]decan-2-yl)butan-2-ylcarbamate (45 mg, 79.4 μmol), methyl (4S,7S)-4-(5-(4-bromophenyl)-1H-imidazol-2-yl)-6,10-dioxooctahydro-1H-pyridazino[1,2-a][1,2]diazepin-7-ylcarbamate (37.8 mg, 79.4 μmol) and sodium bicarbonate (sat solution, 0.4 ml) were combined with tert-butanol (2.6 ml) to give a light brown suspension and deoxygenated for 5 min. PdCl$_2$(DPPF) (5.81 mg, 7.94 μmol) was added and flushed with nitrogen. It was sealed heating at 90° C. for 4 hr. The reaction mixture was diluted with EtOAc (10 ml), filtered and concentrated in vacuo. The residue was purified on a silica gel column (CH$_2$Cl$_2$, 2%, 3%, 5%, 8% MeOH/CH$_2$Cl$_2$) to afford {(4S,7S)-4-[5(4'-{2-[2-((S)-2-Methoxycarbonylamino-3-methyl-butyryl)-8-oxa-2-aza-spiro[4.5]dec-3-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester as a light yellow solid (30 mg, 42.9%). ESI-LRMS m/e calcd for C$_{44}$H$_{53}$N$_9$O$_8$, [M$^+$] 835. found 836 [M+H]. $^1$H NMR (DMSO-d$_6$) δ: 12.09-12.45 (m, 1H), 7.57-7.99 (m, 11H), 7.49 (d, J=8.3 Hz, 2H), 5.80 (br. s., 1H), 4.93-5.16 (m, 1H), 4.46 (d, J=11.3 Hz, 2H), 3.92-4.27 (m, 1H), 3.64 (br. s., 3H), 3.50-3.60 (m, 10H), 2.88 (t, J=10.3 Hz, 1H), 1.77-2.36 (m, 6H), 1.63 (br. s., 2H), 1.48 (d, J=11.5 Hz, 1H), 0.77-1.02 (m, 6H), 0.67 (d, J=6.5 Hz, 2H), 0.12 (d, J=6.8 Hz, 1H).

Example 7

{(4S,7S)-4-[5-(4'-{2-[(S)-1-((S)-2-Methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester ylene chloride and water and the aqueous phase extracted with 20% methanol/methylene chloride. The combined organic phases were washed with a saturated sodium chloride solution and dried over magnesium sulfate, filtered and concentrated. The crude product obtained was purified by reverse phase HPLC using a 50 g Polaris C18A column eluting with acetonitrile/water (30% to 100%) to afford, {(4S,7S)-4-[5-(4'-{2-[(S)-1-((S)-2-methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester as a light yellow solid, (85 mg, 28%): ESI-LRMS m/e calcd for C$_{40}$H$_{47}$N$_9$O$_7$ [M$^+$] 765. found 766 [M+H$^+$]; $^1$H NMR (DMSO-d$_6$) δ: 12.22 (br. s., 1H), 11.76 (br. s., 1H), 7.39-7.88 (m, 10H), 7.29 (d, J=7.8 Hz, 1H), 5.55-5.65 (m, 1H), 5.15-5.25 (m, 1H), 4.50-4.75 (m, 2H), 3.93-4.11 (m, 2H), 3.79 (br. s., 2H), 3.53 (d, J=8.2 Hz, 6H), 2.86 (t, J=10.5 Hz, 1H), 1.81-2.29 (m, 13H), 0.72-0.99 (m, 6H).

Intermediate 1

(S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-ylcarbamate

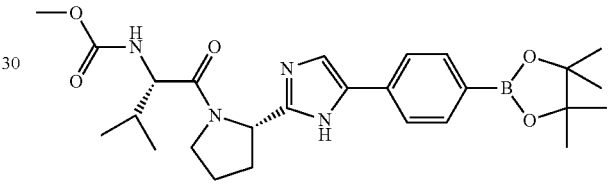

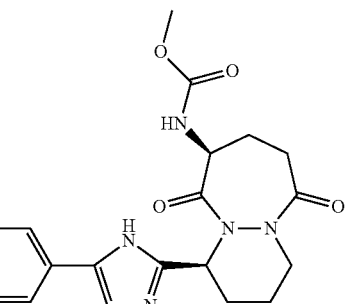

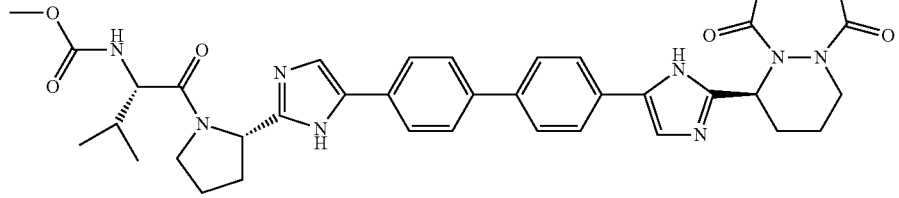

In a sealed tube 1,1'-bis(diphenylphosphino)ferrocene-palladium(II)dichloride (30 mg, 0.04 mmol) was added to a mixture of methyl (S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-ylcarbamate (200 mg, 0.43 mmol) (Intermediate 1), methyl (4S,7S)-4-(5-(4-bromophenyl)-1H-imidazol-2-yl)-6,10-dioxooctahydro-1H-pyridazino[1,2-a][1,2]diazepin-7-ylcarbamate (192 mg, 0.43 mmol) (Intermediate 2) and sodium bicarbonate (102 mg, 0.1.21 mmol) in 1,2-dimethoxyethane (6 ml) and water (1 ml). The reaction mixture was flushed with nitrogen, capped and heated to 80° C. for 16 h. The reaction mixture was concentrated and partitioned between 20% methanol/meth- N,N-Diisopropyethylamine (3.2 g, 24.7 mmol) was added dropwise at room temperature to a heterogeneous mixture of 2-amino-1-(4-bromophenyl)ethanone hydrochloride (2.0 g, 7.98 mmol), (S)-1-(tert-butoxycarbonyl)pyrrolidine-2-carboxylic acid (1.72 g, 7.98 mmol), HATU (3.04 g, 7.98 mmol) and DMF (20 mL). After the addition was complete the reaction mixture was stirred at room temperature for 2 h. The reaction mixture was diluted with ethyl acetate and washed with water, 1N hydrochloric acid, a saturated sodium bicarbonate solution, a saturated sodium chloride solution and dried over magnesium sulfate, filtered and concentrated. The crude product obtained was purified by ISCO flash chromatography (Teledyne Isco RediSep Flash Column 40 g; (0% to 100% ethyl acetatehexane) to afford, (S)-tert-butyl 2-(2-(4-bromophenyl)-2-oxoethylcarbamoyl)pyrrolidine-1-carboxylate as a white solid, (2.50 g, 76%): ESI-LRMS m/e calcd for $C_{18}H_{23}BrN_2O_4$ [M+] 410. found 411 [M+H+].

A mixture of (S)-tert-butyl 2-(2-(4-bromophenyl)-2-oxo-ethylcarbamoyl)pyrrolidine-1-carboxylate (2.50 g, 6.08 mmol) and ammonium acetate (2.34 g, 30.4 mmol) in xylenes (10 mL) was heated in a sealed tube at 140° C. for 4 h. The reaction was then cooled to room temperature and diluted with ethyl acetate. The organic fraction was washed with a saturated sodium bicarbonate solution, a saturated sodium chloride solution and dried over magnesium sulfate, filtered and concentrated. The crude product obtained was purified by ISCO flash chromatography (Teledyne Isco RediSep Flash Column 40 g; (00% to 100% ethyl acetatehexane) to afford, (S)-tert-butyl 2-(5-(4-bromophenyl)-1H-imidazol-2-yl)pyrrolidine-1-carboxylate as a yellow solid, (1.77 g, 74%): ESI-LRMS m/e calcd for $C_{18}H_{22}BrN_3O_2$ [M+] 392. found 393 [M+H+].

A mixture of (S)-tert-butyl 2-(5-(4-bromophenyl)-1H-imidazol-2-yl)pyrrolidine-1-carboxylate (2.45 g, 6.25 mmol) and 4.0 M HCl/dioxane solution (15 mL) in methanol (30 mL) was stirred at room temperature for 4 h. Concentrate the reaction in vacuo. The crude mixture was made basic with saturated sodium bicarbonate solution and was extracted from the aqueous layer with ethyl acetate. The combined organic fractions were washed with a saturated sodium chloride solution and dried over magnesium sulfate, filtered and concentrated to afford, (S)-5-(4-bromophenyl)-2-(pyrrolidin-2-yl)-1H-imidazole hydrochloride as an orange solid, (1.80 g, 98%): ESI-LRMS m/e calcd for $C_{13}H_{14}BrN_3HCl$ [M+] 328.5. found 293 [M+H+] (free base).

N,N-Diisopropylethylamine (2.92 g, 22.6 mmol) was added dropwise at room temperature to a heterogeneous mixture of (S)-5-(4-bromophenyl)-2-(pyrrolidin-2-yl)-1H-imidazole hydrochloride (2.2 g, 7.53 mmol), (S)-2-(methoxycarbonylamino)-3-methylbutanoic acid (1.32 g, 7.53 mmol), HATU (2.86 g, 7.53 mmol) and DMF (20 mL). After the addition was complete the reaction mixture was stirred at room temperature for 5 h. The reaction mixture was diluted with ethyl acetate and washed with water, 1N hydrochloric acid, a saturated sodium bicarbonate solution, a saturated sodium chloride solution and dried over magnesium sulfate, filtered and concentrated. The crude product obtained was purified by ISCO flash chromatography (Teledyne Isco RediSep Flash Column 80 g; (0% to 100% ethyl acetatehexane) to afford, ((S)-1-{(S)-2-[5-(4-bromo-phenyl)-1H-imidazol-2-yl]-pyrrolidine-1-carbonyl}-2-methyl-propyl)-carbamic acid methyl ester as a yellow solid, (2.20 g, 765%): ESI-LRMS m/e calcd for $C_{20}H_{25}BrN_4O_3$ [M+] 449. found 450 [M+H+].

1,1'-bis(diphenylphosphino)ferrocene-palladium(II) dichloride dichloromethane complex (436 mg, 0.53 mmol) was added to a sealed tube containing a mixture of ((S)-1-{(S)-2-[5-(4-bromo-phenyl)-1H-imidazol-2-yl]-pyrrolidine-1-carbonyl}-2-methyl-propyl)-carbamic acid methyl ester (2.40 mg, 5.34 mmol), 4,4,4',4',5,5,5',5'-octamethyl-2,2'-bi(1,3,2-dioxaborolane) (4.07 g, 16.0 mmol), potassium acetate (2.62 mg, 26.7 mmol) and 1,4-dioxane (40 ml). The vessel was purged with nitrogen, capped and heated with an oil bath at 80° C. overnight. Cool the reaction to room temperature and filter through celite. Concentrate the reaction in vacuo. The crude mixture was diluted with methylene chloride and washed with water, a saturated sodium chloride solution and dried over magnesium sulfate, filtered and concentrated. The crude product obtained was purified by ISCO flash chromatography (Teledyne Isco RediSep Flash Column 40 g; (50% to 100% ethyl acetatehexane) to afford, methyl (S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-ylcarbamate as a brown solid, (1.78 g, 67%): ESI-LRMS m/e calcd for $C_{26}H_{37}BN_4O_5$ [M+] 496. found 497 [M+H+].

Intermediate 2

Methyl (4S,7S)-4-(5-(4-bromophenyl)-1H-imidazol-2-yl)-6,10-dioxooctahydro-1H-pyridazino[1,2-a][1,2]diazepin-7-ylcarbamate

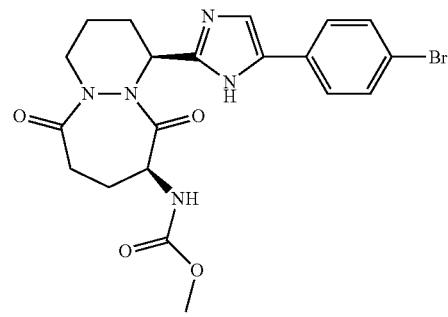 [SMILES: COC(=O)N[C@H]1CCC(=O)N2CCC[C@@H](c3ncc(-c4ccc(Br)cc4)[nH]3)N2C1=O]

To a solution of (1S,9S)-tert-butyl 9-(1,3-dioxoisoindolin-2-yl)-6,10-dioxooctahydro-1H-pyridazino[1,2-a][1,2]diazepine-1-carboxylate (2.00 g, 4.68 mmol) in ethanol (10 mL) was added hydrazine (180 mg, 5.61 mmol). The reaction was stirred at room temperature for 3 h. The ethanol and excess hydrazine were concentrated in vacuo and the residue co-evaporated with ethanol to afford, (1S,9S)-tert-butyl 9-amino-6,10-dioxooctahydro-1H-pyridazino[1,2-a][1,2]diazepine-1-carboxylate as a white powder, (1.63 g, 100%): ESI-LRMS m/e calcd for $C_{14}H_{23}N_3O_4$[M+] 297. found 298 [M+H+].

To an ice-cooled solution of (1S,9S)-tert-butyl 9-amino-6,10-dioxooctahydro-1H-pyridazino[1,2-a][1,2]diazepine-1-carboxylate (1.50 g, 5.04 mmol) in DMF (15 mL) was added sodium carbonate (642 mg, 6.05 mmol) followed by methyl chloroformate (524 mg, 5.55 mmol). After the addition was complete the ice bath was removed and the reaction stirred at room temperature for 2 h. The reaction mixture was diluted with ethyl acetate and washed with water 2N hydrochloric acid, a saturated sodium chloride solution and dried over magnesium sulfate, filtered and concentrated to afford, (1S,9S)-tert-butyl 9-(methoxycarbonylamino)-6,10-dioxooctahydro-1H-pyridazino[1,2-a][1,2]diazepine-1-carboxylate as a white solid, (1.28 g, 71%): ESI-LRMS m/e calcd for $C_{16}H_{25}N_3O_6$[M+] 355. found 356 [M+H+].

To a solution of (1S,9S)-tert-butyl 9-(methoxycarbonylamino)-6,10-dioxooctahydro-1H-pyridazino[1,2-a][1,2]diazepine-1-carboxylate (1.25 g, 3.52 mmol) dissolved into methylene chloride (10 mL) was added trifluoroacetic acid (10 mL). The reaction was stirred at room temperature for 1 h and concentrated in vacuo. Toluene (5 mL) was added and the reaction concentrated in vacuo to afford (1S,9S)-9-(methoxycarbonylamino)-6,10-dioxooctahydro-1H-pyridazino[1,2-a][1,2]diazepine-1-carboxylic acid as a white solid, (587 mg, 68%): ESI-LRMS m/e calcd for $C_{12}H_{17}N_3O_6$[M+] 299. found 300 [M+H+].

N,N'diisopropylethylamine (680 mg, 5.26 mmol) was added dropwise at room temperature to a heterogeneous mixture of (1S,9S)-9-(methoxycarbonylamino)-6,10-dioxooctahydro-1H-pyridazino[1,2-a][1,2]diazepine-1-carboxylic acid (525 mg, 1.75 mmol), 2-amino-1-(4-bromo-phenyl)-ethanone hydrochloride (439 mg, 1.75 mmol), HATU (667 mg, 1.75 mmol) and DMF (10 mL). After addition was complete the reaction was stirred at room temperature for 4 h. The reaction mixture was diluted with ethyl acetate and washed with water, 1N hydrochloric acid, a saturated sodium bicarbonate solution, a saturated sodium chloride solution and dried over magnesium sulfate, filtered and concentrated. The crude product obtained was purified by ISCO flash chromatography (Teledyne Isco RediSep Flash Column 40 g; (30% to 100% ethyl acetatehexane) to afford, methyl (4S,7S)-4-(2-(4-bromophenyl)-2-oxoethylcarbamoyl)-6,10-dioxooctahydro-1H-pyridazino[1,2-a][1,2]diazepin-7-ylcarbamate as a light yellow solid, (587 mg, 68%): ESI-LRMS m/e calcd for $C_{20}H_{23}BrN_4O_6$ [M$^+$] 495. found 496 [M+H$^+$].

A mixture of methyl (4S,7S)-4-(2-(4-bromophenyl)-2-oxoethylcarbamoyl)-6,10-dioxooctahydro-1H-pyridazino[1,2-a][1,2]diazepin-7-ylcarbamate (500 mg, 1.01 mmol) and ammonium acetate (389 mg, 5.05 mmol) in xylenes (10 mL) was heated in a sealed tube at 140° C. for 4 h. The reaction was then cooled to room temperature and diluted with ethyl acetate. The organic fraction was washed with a saturated sodium bicarbonate solution, a saturated sodium chloride solution and dried over magnesium sulfate, filtered and concentrated. The crude product obtained was purified by ISCO flash chromatography (Teledyne Isco RediSep Flash Column 40 g; (30% to 100% ethyl acetatehexane) to afford, methyl (4S,7S)-4-(5-(4-bromophenyl)-1H-imidazol-2-yl)-6,10-dioxooctahydro-1H-pyridazino[1,2-a][1,2]diazepin-7-ylcarbamate as a yellow solid, (435 mg, 91%): ESI-LRMS m/e calcd for $C_{20}H_{22}BrN_5O_4$ [M$^+$] 476. found 477 [M+H$^+$].

Intermediate 3

Methyl (4S,7S)-6,10-dioxo-4-(5-(4-(4,4,5,5-tetramethyl-1,3,2-dioxaborolan-2-yl)phenyl)-1H-imidazol-2-yl)octahydro-1H-pyridazino[1,2-a][1,2]diazepin-7-ylcarbamate

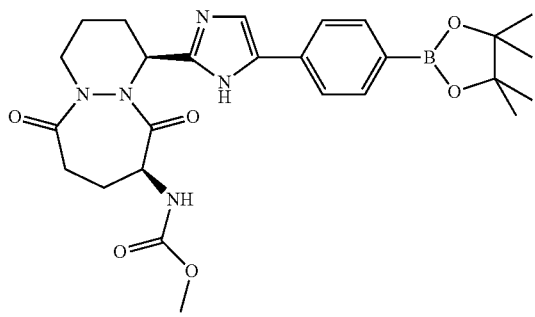 [SMILES: COC(=O)N[C@H]1CCC(=O)N2CCC[C@@H](c3ncc(-c4ccc(B5OC(C)(C)C(C)(C)O5)cc4)[nH]3)N2C1=O]

1,1'-bis(diphenylphosphino)ferrocene-palladium(II) dichloride dichloromethane complex (159 mg, 0.20 mmol) was added to a sealed tube containing a mixture of methyl (4S,7S)-4-(5-(4-bromophenyl)-1H-imidazol-2-yl)-6,10-dioxooctahydro-1H-pyridazino[1,2-a][1,2]diazepin-7-ylcarbamate (925 mg, 1.94 mmol), 4,4,4',4',5,5,5',5'-octamethyl-2,2'-bi(1,3,2-dioxaborolane) (1.48 g, 5.83 mmol), potassium acetate (953 mg, 9.71 mmol) and 1,4-dioxane (40 ml). The vessel was purged with nitrogen, capped and heated with an oil bath at 80° C. overnight. Cool the reaction to room temperature and filter through celite. Concentrate the reaction in vacuo. The crude mixture was diluted with methylene chloride and washed with water, a saturated sodium chloride solution and dried over magnesium sulfate, filtered and concentrated. The crude product obtained was purified by ISCO flash chromatography (Teledyne Isco RediSep Flash Column 40 g; (50% to 100% ethyl acetatehexane) to afford, methyl (4S,7S)-6,10-dioxo-4-(5-(4-(4,4,5,5-tetramethyl-1,3,2-dioxaborolan-2-yl)phenyl)-1H-imidazol-2-yl)octahydro-1H-pyridazino[1,2-a][1,2]diazepin-7-ylcarbamate as a brown solid, (358 mg, 35%): ESI-LRMS m/e calcd for $C_{26}H_{34}BN_5O_6$ [M$^+$] 523. found 524 [M+H$^+$].

Intermediate 4

Methyl(S)-1-((S)-4,4-difluoro-2-(5-(4-(4,4,5,5-tetramethyl-1,3,2-dioxaborolan-2-yl)phenyl)-1H-imidazol-2-yl)pyrrolidin-1-yl)-3-methyl-1-oxobutan-2-yl-carbamate

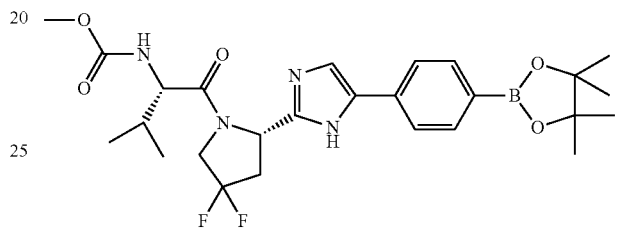

In a 50 mL pear-shaped flask, (S)-1-(tert-butoxycarbonyl)-4,4-difluoropyrrolidine-2-carboxylic acid (1 g, 3.98 mmol, Eq: 1.00) and HATU (1.51 g, 3.98 mmol, Eq: 1.00) were combined with DMF (15 ml) to give a colorless solution and stirred at 23° C. for 10 min. 2-Amino-1-(4-bromophenyl) ethanone HCl (995 mg, 3.98 mmol) was added followed by drop wise addition of DIPEA (1.54 g, 2.09 ml, 11.9 mmol). The suspension became a orange solution once the addition of the amine was completed. It was stirred at room temperature for 1 hr and diluted with brine (100 ml) and H$_2$O (50 ml). The precipitate was filtered, washed with H$_2$O and dried to afford (S)-tert-butyl2-(2-(4-bromophenyl)-2-oxoethylcarbamoyl)-4,4-difluoropyrrolidine-1-carboxylate as a light yellow solid. (1.8 g, >96%): ESI-LRMS m/e calcd for $C_{18}H_{21}BrF_2N_2O_4$ [M$^+$] 447. found 448 [M+H$^+$].

In a 50 mL seal tube, (S)-tert-butyl 2-(2-(4-bromophenyl)-2-oxoethylcarbamoyl)-4,4-difluoropyrrolidine-1-carboxylate (1.8 g, 4.02 mmol) and acetic acid, ammonia acetate salt (1.55 g, 20.1 mmol) were combined with xylene (16 ml). The reaction mixture was heated to 140° C. and stirred for 4 hr. The reaction mixture was cooled and diluted with EtOAc (50 ml). It was washed with water and brine, dried with MgSO$_4$, concentrated and purified on a silica gel column (CH$_2$Cl$_2$, 30%, 50%, 80% EtOAc/CH$_2$Cl$_2$) to afford (S)-tert-butyl 2-(5-(4-bromophenyl)-1H-imidazol-2-yl)-4,4-difluoropyrrolidine-1-carboxylate as a yellow solid (1.77 g, 74%): ESI-LRMS m/e calcd for $C_{18}H_{22}BrF_2N_3O_2$ [M$^+$] 428. found 429 [M+H$^+$].

In a 10 ml pear-shaped flask, (S)-tert-butyl 2-(5-(4-bromophenyl)-1H-imidazol-2-yl)-4,4-difluoropyrrolidine-1-carboxylate (1.0 g, 2.33 mmol) was combined with CH$_2$Cl$_2$ (6 ml) to give a light yellow solution. TFA (2.96 g, 2 mL, 26.0 mmol) was added and stirred for 2 hr. It was concentrated in vacuo to afford (S)-5-(4-bromophenyl)-2-(4,4-difluoropyrrolidin-2-yl)-1H-imidazole as a viscous oil and used for the next step without further purification.

In a 20 ml pear-shaped flask, (S)-2-(methoxycarbonylamino)-3-methylbutanoic acid (416 mg, 2.38 mmol) and HATU (695 mg, 1.83 mmol) were combined with DMF (10 ml) to give a colorless solution. (S)-5-(4-bromophenyl)-2-(4,4-difluoropyrrolidin-2-yl)-1H-imidazole (600 mg, 1.83 mmol) in 2 ml of DMF was added and followed by drop wise addition of DIPEA (1.18 g, 1.6 ml, 9.14 mmol). It was stirred at room temperature for 1 hr then poured into ice/water. It was extracted with EtOAc (2×30 ml), washed with brine and water. The organic layer was dried over MgSO$_4$, concentrated and purified on a silica gel column (CH$_2$Cl$_2$, 1%, 2%, 5% MeOH/CH$_2$Cl$_2$) to afford methyl (S)-1-((S)-2-(5-(4-bromophenyl)-1H-imidazol-2-yl)-4,4-difluoropyrrolidin-1-yl)-3-methyl-1-oxobutan-2-yl-carbamate as an orange foaming solid. (650 mg, 73%): ESI-LRMS m/e calcd for C$_{20}$H$_{25}$BrF$_2$N$_4$O$_3$ [M$^+$] 485. found 486 [M+H$^+$].

In a 20 mL seal tube, methyl (S)-1-((S)-2-(5-(4-bromophenyl)-1H-imidazol-2-yl)-4,4-difluoropyrrolidin-1-yl)-3-methyl-1-oxobutan-2-yl-carbamate (300 mg, 618 μmol), 4,4,4',4',5,5,5',5'-octamethyl-2,2'-bi(1,3,2-dioxaborolane) (471 mg, 1.85 mmol) and potassium acetate (303 mg, 3.09 mmol) were combined with 1,4-dioxane (6 ml) to give a light yellow suspension. It was degassed for 20 min. 1,1'-Bis(diphenylphosphino)ferrocene-palladium(II)dichloride dichloromethane complex (50.5 mg, 61.8 μmol) was added, flushed with N$_2$, sealed heating at 80° C. for 16 hr. It was cooled and diluted with EtOAc (40 ml). The mixture was washed with brine and water, dried with MgSO$_4$, concentrated and purified on a silica gel column (CH$_2$Cl$_2$, 1%, 2%, 3% to 5% MeOH/CH$_2$Cl$_2$) to afford methyl (S)-1-((S)-4,4-difluoro-2-(5-(4-(4,4,5,5-tetramethyl-1,3,2-dioxaborolan-2-yl)phenyl)-1H-imidazol-2-yl)pyrrolidin-1-yl)-3-methyl-1-oxobutan-2-yl-carbamate as an orange solid. (300 mg, 87%): ESI-LRMS m/e calcd for C$_{26}$H$_{37}$BF$_2$N$_4$O$_5$ [M$^+$] 532. found 533 [M+H$^+$].

Intermediate 5

Methyl(S)-3-methyl-1-oxo-1-((S)-8-(5-(4-(4,4,5,5-tetramethyl-1,3,2-dioxaborolan-2-yl)phenyl)-1H-imidazol-2-yl)-1,4-dioxa-7-azaspiro[4.4]nonan-7-yl)butan-2-ylcarbamate

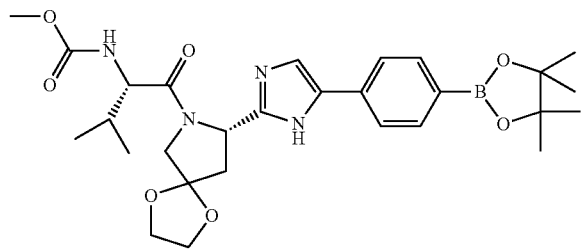

In a 500 mL round-bottomed flask, (S)-2-(methoxycarbonylamino)-3-methylbutanoic acid (2.90 g, 16.6 mmol) and HATU (6.29 g, 16.6 mmol) were combined with CH$_2$Cl$_2$ (300 ml) to give a colorless suspension. TEA (5.03 g, 6.92 ml, 49.7 mmol) was added and stirred at rt for 30 min. (2S,4R)-methyl 4-hydroxypyrrolidine-2-carboxylate HCl (3.01 g, 16.6 mmol) was added and stirred at room temperature for 5 hr. It was diluted with NaHCO$_3$ (sat. solution, 100 ml) and organic phase was separated. The aqueous layer was extracted with CH$_2$Cl$_2$ (2×100 ml) and the organic layer was dried with MgSO$_4$, filtered and concentrated in vacuo. The crude material was purified by a silica gel column (CH$_2$Cl$_2$, 20%, 40%, 60%, 80% EtOAc/CH$_2$Cl$_2$) to afford (2S,4R)-methyl 4-hydroxy-1-((S)-2-(methoxycarbonylamino)-3-methylbutanoyl)pyrrolidine-2-carboxylate as an oil (4.0 g, 79.9%). $^1$H NMR (400 MHz, DMSO-d$_6$) δ ppm 0.88 (dd, J=17.32, 6.78 Hz, 17H) 1.75-1.96 (m, 5H) 2.10 (br. s., 3H) 3.46-3.62 (m, 16H) 3.63-3.77 (m, 5H) 4.33 (d, J=8.03 Hz, 5H) 5.21 (d, J=3.76 Hz, 3H) 7.30 (d, J=8.78 Hz, 2H)

In a 100 mL round-bottomed flask, (2S,4R)-methyl 4-hydroxy-1-((S)-2-(methoxycarbonylamino)-3-methylbutanoyl)pyrrolidine-2-carboxylate (0.8 g, 2.65 mmol) was combined with CH$_2$Cl$_2$ (20 ml) to give a colorless solution. Dess-Martin periodinane (2.24 g, 5.29 mmol) was added and stirred at room temperature for 2 hr. It was quenched with 5% sodium thiosulfate (80 ml), NaHCO$_3$ (sat. solution 100 ml) and stirred for 20 min. The reaction mixture was extracted with CH$_2$Cl$_2$ (2×100 ml) and the combined organic layers were dried with MgSO$_4$, filtered and concentrated in vacuo. The crude product was purified on a silica gel column (CH$_2$Cl$_2$, 20%, 40%, 60% EtOAc/CH$_2$Cl$_2$) to afford (methoxycarbonylamino)-3-methylbutanoyl)-4-oxopyrrolidine-2-carboxylate as a colorless oil (230 mg, 28.9%). $^1$H NMR (400 MHz, CHLOROFORM-d) δ ppm 0.91-1.11 (m, 24H) 1.97-2.11 (m, 10H) 2.56-2.76 (m, 4H) 2.87-3.09 (m, 4H) 3.67 (s, 12H) 3.77 (s, 12H) 4.33-4.58 (m, 3H) 5.03-5.16 (m, 3H) 5.21-5.51 (m, 3H)

In a 50 mL round-bottomed flask, (S)-methyl 1-((S)-2-(methoxycarbonylamino)-3-methylbutanoyl)-4-oxopyrrolidine-2-carboxylate (230 mg, 766 μmol, Eq: 1.00) and ethane-1,2-diol (238 mg, 214 μl, 3.83 mmol, Eq: 5) were combined with toluene (15 ml) to give a colorless solution. p-toluenesulfonic acid monohydrate (29.1 mg, 153 μmol) was added and the reaction mixture was heated to 110° C. with a Dean-Stark apparatus for 20 hr. After cooling, it was diluted with EtOAc (50 ml), washed with NaHCO$_3$ (sat solution, 200 ml), dried and concentrated in vacuo. The crude mixture was purified on a silica gel column (CH$_2$Cl$_2$, 20%, 30%, 40% and 60% EtOAc/CH$_2$Cl$_2$) to afford (S)-methyl 7-((S)-2-(methoxycarbonylamino)-3-methylbutanoyl)-1,4-dioxa-7-azaspiro[4.4]nonane-8-carboxylate as an oil (110 mg, 41.7%). $^1$H NMR (400 MHz, CHLOROFORM-d) δ ppm 0.95 (d, J=6.78 Hz, 8H) 1.05 (d, J=6.78 Hz, 7H) 1.57 (s, 2H) 2.22 (dd, J=13.18, 6.90 Hz, 3H) 2.37 (dd, J=13.05, 8.78 Hz, 2H) 3.62-3.70 (m, 11H) 3.71-3.87 (m, 10H) 3.93-4.03 (m, 11H) 4.25 (d, J=2.76 Hz, 4H) 4.59-4.78 (m, 2H) 5.23-5.51 (m, 2H) 5.26-5.51 (m, 2H)

In a 10 mL round-bottomed flask, (S)-methyl 7-((S)-2-(methoxycarbonylamino)-3-methylbutanoyl)-1,4-dioxa-7-azaspiro[4.4]nonane-8-carboxylate (150 mg, 436 μmol) was combined with tert-butanol (250 μl) to give a colorless solution. LiOH (1M, 871 μl, Eq: 2) was added and stirred at room temperature for 2 hr. It was acidified with 1N HCl to pH 3 and diluted with 100 ml of EtOAc. It was washed with brine (5 ml), dried with MgSO$_4$, filtered and concentrated in vacuo to afford (S)-7-((S)-2-(methoxycarbonylamino)-3-methylbutanoyl)-1,4-dioxa-7-azaspiro[4.4]nonane-8-carboxylic acid as a white solid which was used for the next reaction without further purification. (75 mg, 52.1%).

In a 50 mL flask, (S)-7-((S)-2-(methoxycarbonylamino)-3-methylbutanoyl)-1,4-dioxa-7-azaspiro[4.4]nonane-8-carboxylic acid (110 mg, 333 μmol) was combined with DMF (5.00 ml) to give a colorless solution. HATU (127 mg, 333 μmol) was added and stirred at room temperature for 10 min followed by addition of 2-amino-1-(4-bromophenyl)ethanone HCl (83.3 mg, 333 μmol, Eq: 1.00). DIPEA (129 mg, 174 μl, 999 μmol) was then added dropwise and the suspension became a yellow solution once the DIPEA was added. It was stirred at room temperature for 1 hr then poured into brine solution (80 ml). The precipitate was filtered and washed with $H_2O$ then dissolved in $CH_2Cl_2$ (50 ml), It was dried with $MgSO_4$, filtered and concentrated in vacuo to afford methyl (S)-1-((S)-8-(2-(4-bromophenyl)-2-oxoethylcarbamoyl)-1,4-dioxa-7-azaspiro[4.4]nonan-7-yl)-3-methyl-1-oxobutan-2-ylcarbamate as a yellow solid (75 mg, 42.8%). ESI-LRMS m/e calcd for $C_{22}H_{28}BrN_3O_7$ [M+] 526. found 527 [M+H+].

In a 5 mL seal tube, methyl (S)-1-((S)-8-(2-(4-bromophenyl)-2-oxoethylcarbamoyl)-1,4-dioxa-7-azaspiro[4.4]nonan-7-yl)-3-methyl-1-oxobutan-2-ylcarbamate (75 mg, 142 µmol) was combined with 1,4-dioxane (2 ml) to give a light yellow solution. Ammonium acetate (110 mg, 1.42 mmol) was added and it was stirred at 110° C. overnight. It was cooled and diluted with EtOAc(10 ml), filtered and concentrated in vacuo to afford methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate as a light brownish solid (70 mg, 96.8%). ESI-LRMS m/e calcd for $C_{22}H_{27}BrN_4O_5$ [M+] 507. found 508 [M+H+].

In a 20 mL seal tube, methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate (70 mg, 138 µmol), 4,4,4',4',5,5,5',5'-octamethyl-2,2'-bi(1,3,2-dioxaborolane) (105 mg, 414 µmol) and potassium acetate (67.7 mg, 690 µmol, Eq: 5.0) were combined with 1,4-dioxane (2 ml) to give a light yellow suspension. It was degassed for 20 min and 1,1'-bis(diphenylphosphino)ferrocene-palladium(II)dichloride dichloromethane complex (11.3 mg, 13.8 µmol) was added. It was flushed with $N_2$, sealed and stirred at 80° C. for 16 hr. The reaction mixture was cooled and diluted with EtOAc (10 ml). It was filtered through celite, concentrated in vacuo and purified on a silica gel column ($CH_2Cl_2$, 1%, 2%, 3% to 5% $MeOH/CH_2Cl_2$) to afford methyl (S)-3-methyl-1-oxo-1-((S)-8-(5-(4-(4,4,5,5-tetramethyl-1,3,2-dioxaborolan-2-yl)phenyl)-1H-imidazol-2-yl)-1,4-dioxa-7-azaspiro[4.4]nonan-7-yl)butan-2-ylcarbamate as a light brownish solid. (31 mg, 41.5%). ESI-LRMS m/e calcd for $C_{28}H_{39}BN_4O_7$ [M+] 554. found 555 [M+H+].

Intermediate 6

Methyl(2S)-3-methyl-1-oxo-1-(3-(5-(4-(4,4,5,5-tetramethyl-1,3,2-dioxaborolan-2-yl)phenyl)-1H-imidazol-2-yl)-8-oxa-2-azaspiro[4.5]decan-2-yl)butan-2-ylcarbamate

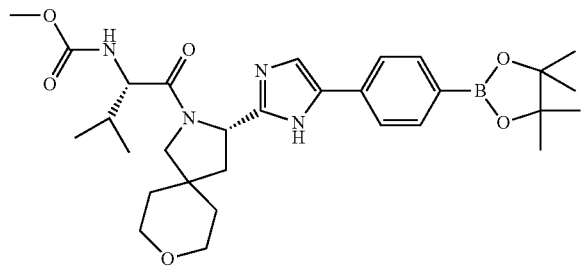

In a 50 ml round-bottomed flask, (S)-2-(methoxycarbonylamino)-3-methylbutanoic acid (813 mg, 4.64 mmol) was combined with DMF (10 ml) to give a colorless solution. HATU (1.76 g, 4.64 mmol) was added and stirred at room temperature for 10 min. Ethyl 8-oxa-2-azaspiro[4.5]decane-3-carboxylate (prepared according to the patent procedure described in WO 199808850) (900 mg, 4.22 mmol) and DIPEA (1.91 g, 2.58 ml, 14.8 mmol) were added and stirred overnight. It was diluted with $H_2O$ and extracted with EtOAc (2×100 ml). The organic layer was washed with brine and $H_2O$, dried with $MgSO_4$, filtered and concentrated in vacuo to afford (S)-ethyl 2-((S)-2-(methoxycarbonylamino)-3-methylbutanoyl)-8-oxa-2-azaspiro[4.5]decane-3-carboxylate as a viscous oil (1.3 g, 83.2%). ESI-LRMS m/e calcd for $C_{18}H_{30}N_2O_6$ [M+] 370. found 371 [M+H+].

In a 10 mL round-bottomed flask, (S)-ethyl 2-((S)-2-(methoxycarbonylamino)-3-methylbutanoyl)-8-oxa-2-azaspiro[4.5]decane-3-carboxylate (300 mg, 810 µmol) was combined with THF 6(ml) and tert-butanol (1 ml) to give a colorless solution. LiOH (1.0M, 1.62 ml, 1.62 mmol, Eq: 2) was added and stirred at room temperature for 2 hr. Then more LiOH (1.0M, 1 ml, 1 mmol) was added and stirred for an another 2 hr. THF was removed and the aqueous was acidified with 1N HCl to pH=3 and diluted with EtOAc (100 ml). It was washed with brine (10 ml), dried with $MgSO_4$, filtered and concentrated to afford 2-((S)-2-(methoxycarbonylamino)-3-methylbutanoyl)-8-oxa-2-azaspiro[4.5]decane-3-carboxylic acid as a white solid (270 mg, 97.4%). ESI-LRMS m/e calcd for $C_{16}H_{26}N_2O_6$ [M+] 342. found 341 [M+H+].

In a 50 mL flask, 2-((S)-2-(methoxycarbonylamino)-3-methylbutanoyl)-8-oxa-2-azaspiro[4.5]decane-3-carboxylic acid (200 mg, 584 µmol) was combined with DMF (5.00 ml) to give a colorless solution. HATU (222 mg, 584 µmol) was added and stirred at room temperature for 10 min followed by addition of 2-amino-1-(4-bromophenyl)ethanone HCl (146 mg, 584 µmol). DIPEA (264 mg, 357 µl, 2.04 mmol) was then added dropwise and the suspension became a yellow solution once the DIPEA was added. It was stirred at room temperature for 1 hr and poured into brine solution (80 ml) and extracted with EtOAc (2×60 ml). The organic layer was washed with brine and $H_2O$, dried with $MgSO_4$, filtered and concentrated in vacuo to give a yellow solid. It was purified on a silica gel column ($CH_2Cl_2$, 2%, 4%, 6% $MeOH/CH_2Cl_2$) to afford methyl (2S)-1-(3-(2-(4-bromophenyl)-2-oxoethylcarbamoyl)-8-oxa-2-azaspiro[4.5]decan-2-yl)-3-methyl-1-oxobutan-2-ylcarbamate as a solid (200 mg, 63.6%). ESI-LRMS m/e calcd for $C_{24}H_{32}BrN_3O_6$ [M+] 538. found 539 [M+H+].

In a 10 ml seal tube, methyl (2S)-1-(3-(2-(4-bromophenyl)-2-oxoethylcarbamoyl)-8-oxa-2-azaspiro[4.5]decan-2-yl)-3-methyl-1-oxobutan-2-ylcarbamate (200 mg, 371 µmol) was combined with dioxane (6 ml) to give a colorless solution. Ammonium acetate (286 mg, 3.71 mmol) was added and it was stirred at 110° C. overnight. It was cooled and diluted with EtOAc (10 ml). The mixture was filtered and concentrated in vacuo to afford methyl (2S)-1-(3-(5-(4-bromophenyl)-1H-imidazol-2-yl)-8-oxa-2-azaspiro[4.5]decan-2-yl)-3-methyl-1-oxobutan-2-ylcarbamate as a yellow solid (170 mg, 88.1%). ESI-LRMS m/e calcd for $C_{24}H_{31}BrN_4O_4$ [M+] 519. found 520 [M+H+].

In a 20 mL seal tube, methyl (2S)-1-(3-(5-(4-bromophenyl)-1H-imidazol-2-yl)-8-oxa-2-azaspiro[4.5]decan-2-yl)-3-methyl-1-oxobutan-2-ylcarbamate (170 mg, 327 µmol), 4,4,4',4',5,5,5',5'-octamethyl-2,2'-bi(1,3,2-dioxaborolane) (249 mg, 982 µmol) and potassium acetate (161 mg, 1.64 mmol) were combined with 1,4-dioxane (2.00 ml) to give a light yellow suspension. It was degassed for 20 min. 1,1'-Bis(diphenylphosphino)ferrocene-palladium(II)dichloride dichloromethane complex (26.7 mg, 32.7 µmol) was added, flushed with $N_2$. It was sealed and stirred at 80° C. for 16 hr, then cooled and diluted with EtOAc (40 ml). The reaction mixture was filtered through celite, concentrated in vacuo and purified on a silica gel column ($CH_2Cl_2$, 1%, 2%, 3% to 5% MeOH/$CH_2Cl_2$) to afford methyl (2S)-3-methyl-1-oxo-1-(3-(5-(4-(4,4,5,5-tetramethyl-1,3,2-dioxaborolan-2-yl)phenyl)-1H-imidazol-2-yl)-8-oxa-2-azaspiro[4.5]decan-2-yl)butan-2-ylcarbamate as a light brown solid (110 mg, 59.3%). ESI-LRMS m/e calcd for $C_{30}H_{43}BN_4O_6$ [M+] 566. found 567 [M+H+].

Intermediate 7

Benzyl(4S,7S)-4-(5-(4-bromophenyl)-1H-imidazol-2-yl)-6,10-dioxooctahydro-1H-pyridazino[1,2-a][1,2]diazepin-7-ylcarbamate

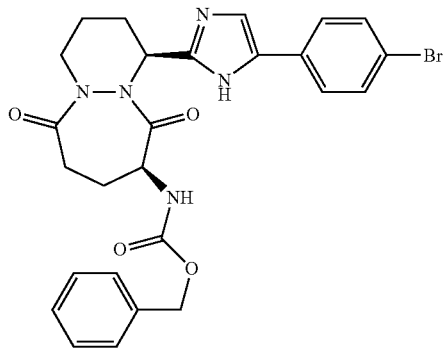 [SMILES: O=C(N[C@H]1CCC(=O)N2CCC[C@@H](c3ncc(-c4ccc(Br)cc4)[nH]3)N2C1=O)OCc1ccccc1]

In a 200 mL round-bottomed flask, (1S,9S)-tert-butyl 9-(1,3-dioxoisoindolin-2-yl)-6,10-dioxooctahydro-1H-pyridazino[1,2-a][1,2]diazepine-1-carboxylate (5 g, 11.7 mmol) was combined with ethanol (50 ml) to give a colorless suspension. Hydrazine (825 mg, 808 µl, 25.7 mmol) was added and stirred at room temperature for 2 hr. The crude reaction mixture was concentrated in vacuo and evaporated with toluene. 2M aqueous acetic acid (50 ml) was added and stirred at room temperature overnight. The precipitate was filtered and the filtrate was basified with sodium carbonate solution. It was extracted with $CH_2Cl_2$ (2×150 ml). The combined organic layer was dried with $MgSO_4$ and concentrated in vacuo to afford (1S,9S)-tert-butyl 9-amino-6,10-dioxooctahydro-1H-pyridazino[1,2-a][1,2]diazepine-1-carboxylate as a sticky white solid (3.4 g, 97.8%). ESI-LRMS m/e calcd for $C_{14}H_{23}N_3O_4$ [M+] 297. found 298 [M+H+].

In a 20 mL pear-shaped flask, (1S,9S)-tert-butyl 9-amino-6,10-dioxooctahydro-1H-pyridazino[1,2-a][1,2]diazepine-1-carboxylate (0.9 g, 3.03 mmol) was combined with DMF (8 ml) to give a colorless solution and cooled to 0° C. Sodium carbonate (385 mg, 3.63 mmol) and benzyl carbonochloridate (516 mg, 432 µl, 3.03 mmol) were added and stirred at room temperature for 6 hr. It was diluted with brine and $H_2O$, extracted with EtOAc (2×60 ml). The combined organic layer was washed with brine and $H_2O$, dried with $MgSO_4$, filtered and concentrated in vacuo to afford (1S,9S)-tert-butyl-9-(benzyloxycarbonylamino)-6,10-dioxooctahydro-1H-pyridazino[1,2-a][1,2]diazepine-1-carboxylate as an oil (1.3 g, 99.5%). ESI-LRMS m/e calcd for $C_{18}H_{21}N_3O_6$ [M+] 431. found 432 [M+H+]. The crude was used without further purification.

In a 10 mL round-bottomed flask, (1S,9S)-tert-butyl 9-(benzyloxycarbonylamino)-6,10-dioxooctahydro-1H-pyridazino[1,2-a][1,2]diazepine-1-carboxylate (1.3 g, 3.01 mmol) was combined with $CH_2Cl_2$ (5 ml) to give a colorless solution. TFA (3.53 g, 2.38 ml, 31.0 mmol) was added and stirred at room temperature for 5 hr. The crude reaction mixture was concentrated in vacuo and redissolved in EtOAc (10 ml). It was evaporated to afford (1S,9S)-9-(benzyloxycarbonylamino)-6,10-dioxooctahydro-1H-pyridazino[1,2-a][1,2]diazepine-1-carboxylic acid as a foaming solid (1.0 g, 88.4%).

ESI-LRMS m/e calcd for $C_{18}H_{21}N_3O_6$ [M+] 375. found 376 [M+H+].

In a 50 ml, round-bottomed flask, (1S,9S)-9-(benzyloxycarbonylamino)-6,10-dioxo octahydro-1H-pyridazino[1,2-a][1,2]diazepine-1-carboxylic acid (1 g, 2.66 mmol) was combined with DMF (15 ml) to give a colorless solution. HATU (1.01 g, 2.66 mmol) was added and stirred at room temperature for 10 min. 2-Amino-1-(4-bromophenyl)ethanone HCl (666 mg, 2.66 mmol, Eq: 1.00) and DIPEA (1.03 g, 1.4 ml, 7.99 mmol) were added and stirred at room temperature overnight. The reaction mixture was diluted with brine and $H_2O$ and extracted with EtOAc (2×60 ml). The organic layers were combined, washed with brine (2×20 mL), $H_2O$ (2×50 mL), dried with $MgSO_4$ and concentrated in vacuo. The crude product was purified on a silica gel column ($CH_2Cl_2$, 2%, 3%, 5%, 6%, 8% MeOH/$CH_2Cl_2$) to afford benzyl (4S,7S)-4-(2-(4-bromophenyl)-2-oxoethylcarbamoyl)-6,10-dioxooctahydro-1H-pyridazino[1,2-a][1,2]diazepin-7-ylcarbamate as a light yellow solid (1.2 g, 78.8%). ESI-LRMS m/e calcd for $C_{26}H_{27}BrN_4O_6$ [M+] 571. found 572 [M+H+].

In a 10 ml, seal tube, benzyl (4S,7S)-4-(2-(4-bromophenyl)-2-oxoethylcarbamoyl)-6,10-dioxooctahydro-1H-pyridazino[1,2-a][1,2]diazepin-7-ylcarbamate (200 mg, 350 µmol) was combined with 1,4-dioxane (5 ml) to give a light yellow solution. Ammonium acetate (270 mg, 3.5 mmol) was added and the reaction mixture was heated at 110° C. for 12 hr. It was cooled and diluted with EtOAc (2×30 ml). The combined organic layers were washed with brine and $H_2O$, dried with $MgSO_4$ and concentrated in vacuo to afford a viscous oil. The crude was purified on a silica gel column ($CH_2Cl_2$, 2%, 4%, 6%, 8% MeOH/$CH_2Cl_2$) to afford benzyl (4S,7S)-4-(5-(4-bromophenyl)-1H-imidazol-2-yl)-6,10-dioxooctahydro-1H-pyridazino[1,2-a][1,2]diazepin-7-ylcarbamate as a yellow solid (66 mg, 34.1%). ESI-LRMS m/e calcd for $C_{26}H_{26}BrN_5O_4$ [M+] 552. found 553 [M+H+].

Intermediate 8

Methyl(4S,7S)-6,10-dioxo-4-(5-(4-(6-(2-((8)-pyrrolidin-2-yl)-1H-imidazol-5-yl)quinoxalin-2-yl)phenyl)-1H-imidazol-2-yl)octahydro-1H-pyridazino[1,2-a][1,2]diazepin-7-ylcarbamate

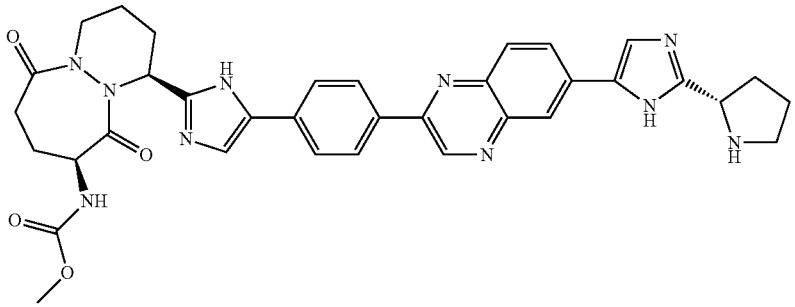 [SMILES: COC(=O)N[C@H]1CCC(=O)N2CCC[C@@H](c3ncc(-c4ccc(-c5cnc6cc(-c7cnc([C@@H]8CCCN8)[nH]7)ccc6n5)cc4)[nH]3)N2C1=O]

In a 10 ml seal tube, methyl (4S,7S)-6,10-dioxo-4-(5-(4-(4,4,5,5-tetramethyl-1,3,2-dioxaborolan-2-yl)phenyl)-1H-imidazol-2-yl)octahydro-1H-pyridazino[1,2-a][1,2]diazepin-7-ylcarbamate (240 mg, 459 μmol) (Intermediate 3), 6-bromo-2-chloroquinoxaline (112 mg, 459 μmol) and $Cs_2CO_3$ (299 mg, 917 μmol) were combined with 1,4-dioxane (3.00 ml) and water (0.5 ml) to give a light brown solution. It was degassed for 10 min and tetrakis(triphenylphosphine)palladium (0) (53.0 mg, 45.9 μmol) was added. The reaction mixture was heated at 80° C. for 16 h. It was diluted with EtOAc (6 ml) and concentrated in vacuo. The residue was purified on a silica gel column ($CH_2Cl_2$, 2%, 3%, 5%, 8% and 10% MeOH/$CH_2Cl_2$) to afford methyl (4S,7S)-4-(5-(4-(6-bromoquinoxalin-2-yl)phenyl)-1H-imidazol-2-yl)-6,10-dioxooctahydro-1H-pyridazino[1,2-a][1,2]diazepin-7-ylcarbamate as a red solid (240 mg, 86.6%). ESI-LRMS m/e calcd for $C_{28}H_{26}BrN_7O_4$ [M+] 604. found 605 [M+H+].

In a 20 mL seal tube, methyl (4S,7S)-4-(5-(4-(6-bromoquinoxalin-2-yl)phenyl)-1H-imidazol-2-yl)-6,10-dioxooctahydro-1H-pyridazino[1,2-a][1,2]diazepin-7-ylcarbamate (230 mg, 381 μmol), 4,4,4',4',5,5,5',5'-octamethyl-2,2'-bi(1,3,2-dioxaborolane) (290 mg, 1.14 mmol) and potassium acetate (187 mg, 1.9 mmol) were combined with 1,4-dioxane (9.6 ml) to give a light yellow suspension. It was degassed for 20 min and 1,1' bis(diphenylphosphino)ferrocene-palladium(II) dichloride dichloro methane complex (31.1 mg, 38.1 μmol) was added. It was flushed with $N_2$, sealed and stirred at 80° C. for 3 hr, then cooled and diluted with EtOAc (40 ml). The organic layer was washed with brine and water, dried with $MgSO_4$, filtered, concentrated in vacuo and purified on a silica gel column ($CH_2Cl_2$, 1%, 2%, 3% to 5%, 10% MeOH/$CH_2Cl_2$) to afford methyl (4S,7S)-6,10-dioxo-4-(5-(4-(6-(4,4,5,5-tetramethyl-1,3,2-dioxaborolan-2-yl)quinoxalin-2-yl)phenyl)-1H-imidazol-2-yl)octahydro-1H-pyridazino[1,2-a][1,2]diazepin-7-ylcarbamate as a brown solid (140 mg, 56.5%). ESI-LRMS m/e calcd for $C_{34}H_{38}BN_7O_6$ [M+] 651. found 652 [M+H+].

In a 10 mL seal tube, methyl (4S,7S)-6,10-dioxo-4-(5-(4-(6-(4,4,5,5-tetramethyl-1,3,2-dioxaborolan-2-yl)quinoxalin-2-yl)phenyl)-1H-imidazol-2-yl)octahydro-1H-pyridazino[1,2-a][1,2]diazepin-7-ylcarbamate (66.0 mg, 101 μmol, Eq: 1.00), (S)-tert-butyl 2-(5-iodo-1-((2-(trimethylsilylepthoxy)methyl)-1H-imidazol-2-yl)pyrrolidine-1-carboxylate (50 mg, 101 μmol) (Milbank, J. et al, WO2011004276 A1) and $Cs_2CO_3$ (66.0 mg, 203 μmol) were combined with 1,4-dioxane (2.00 ml) and water (0.5 ml) to give a light brown suspension. It was degassed for 10 min and tetrakis(triphenylphosphine)palladium (0) (11.7 mg, 10.1 μmol) was added. The reaction mixture was heated to 80° C. and stirred for 16 hr. It was diluted with EtOAc (6 ml) and concentrated in vacuo. The residue was purified on a silica gel column ($CH_2Cl_2$, 2%, 3%, 5%, 8% and 10% MeOH/$CH_2Cl_2$) to afford (S)-tert-butyl 2-(5-(2-(4-(2-((1S,9S)-9-(methoxycarbonylamino)-6,10-dioxooctahydro-1H-pyridazino[1,2-a][1,2]diazepin-1-yl)-1H-imidazol-5-yl)phenyl)quinoxalin-6-yl)-1-((2-(trimethylsilylepthoxy)methyl)-1H-imidazol-2-yl)pyrrolidine-1-carboxylate as a yellow solid (62 mg, 68.7%). ESI-LRMS m/e calcd for $C_{46}H_{58}N_{10}O_7Si$ [M+] 891. found 892 [M+H+].

In a 10 mL pear-shaped flask, (S)-tert-butyl 2-(5-(2-(4-(2-((1S,9S)-9-(methoxycarbonyl amino)-6,10-dioxooctahydro-1H-pyridazino[1,2-a][1,2]diazepin-1-yl)-1H-imidazol-5-yl)phenyl)quinoxalin-6-yl)-1-((2-(trimethylsilylepthoxy)methyl)-1H-imidazol-2-yl)pyrrolidine-1-carboxylate (30 mg, 33.7 μmol) was combined with EtOH (4 ml) to give an orange solution. 4N HCl in 1,4-dioxane (1.68 ml, 6.73 mmol) was added and stirred at 62° C. overnight. The crude reaction mixture was concentrated in vacuo and diluted with $Et_2O$. The precipitate was collected, washed with $Et_2O$, and dried to afford methyl (4S,7S)-6,10-dioxo-4-(5-(4-(6-(2-((S)-pyrrolidin-2-yl)-1H-imidazol-5-yl)quinoxalin-2-yl)phenyl)-1H-imidazol-2-yl)octahydro-1H-pyridazino[1,2-a][1,2]diazepin-7-ylcarbamate as an orange solid (21 mg, 94.4%). ESI-LRMS m/e calcd for $C_{35}H_{36}N_{10}O_4$ [M+] 660. found 661 [M+H+].

Biological Examples

Determination of compounds HCV GT1b inhibitory replicon activity using the replicon luciferase reporter assay The 2209-23 cell line was developed at Roche by stable transfection of the hepatoma cell line Huh-7 with a GT-1b Con1 subgenomic bicistronic replicon as previously described. Subgenomic replicon cell line was established in cured Huh7 cells, obtained from R. Bartenschlager (J Virol. 2003 March; 77 (5):3007-19) The GT-1a H77 subgenomic replicon vector pRLuc H77 1b 75 SI, was created by replacing the non structural region of the GT-1b Con1 subgenomic replicon by the one of the H77 strain, except for the first 75 amino acids of the NS3 protein that are from GT-1b Con1 strain. (J Virol. 2001 77:5352-59) The GT-1a pRLuc H77 1b 75 SI subgenomic replicon cell line was established in cured Huh7 cells, obtained from R. Bartenschlager. (J Virol. 2003 March; 77 (5):3007-19)

All the subgenomic replicon cell lines were cultured in Dulbecco's Modified Eagle Medium (DMEM-Glutamax™-

I; Invitrogen Cat #10569-010). The medium was supplemented with 10% Fetal Bovine Serum (Invitrogen Cat #10082-147), 1% penicillin/streptomycin (Mediatech Cat #30-002-CI) and 500 µg/ml of G418 (Mediatech Cat #30-234-CI). Cells were maintained at 37° C. in a humidified 5% $CO_2$ atmosphere.

2209-23 cells were plated at a cell density of 5000 cells per well in 96 well plates (Becton Dickinson, Cat #35 3296). Cells were plated in 90 µl of Dulbecco's Modified Eagle Medium (DMEM-Glutamax™-I), (Invitrogen Cat #10569-010) medium was supplemented with 5% Fetal Bovine Serum (Invitrogen Cat #10082-147), 1% penicillin/streptomycin (Mediatech Cat #30-002-CI). The pRluc H77 1b 75 SI cells were plated in 96-well plate at 3000 cells/well in DMEM-Glutamax™-I containing 5% FBS and 1% penicillin/streptomycin in 90 µl final volume. Cells were allowed to equilibrate for 24 hours at 37° C. and 5% CO2 at which time compounds were added. Compounds (or medium as a control) were added 24 hours post-plating in 3 fold dilutions at a final DMSO concentration of 1% in 10 ul volume. Renilla luciferase reporter signal was read 72 hours after addition of compounds using the Renilla Luciferase Assay System (Promega, cat # E2820). EC50 values were defined as the compound concentration at which a 50% reduction in the levels of renilla luciferase reporter was observed as compared to control samples in the absence of compound and was determined by non-linear fitting of compound dose-response data. The EC50 was approximated if maximum percentage inhibition was less than 90% and more than 70%.

Determination of Compounds Cytotoxicity Using the HCV GT1b Replicon Cell Line Measuring WST1.

2209-23 cells were plated at a cell density of 5000 cells per well in clear flat-bottom 96 well plate (Becton Dickinson, Cat #35 3075) for cell viability studies. The WST-1 cell proliferation assay (Roche Diagnostic, Cat#11644807001) was used to determine cell viability. Assay plates were set up in the same format as in the replicon assay. After 3 days of compound incubation 10 µl of WST-1 reagent was added to each well for 2 hours at 37° C. and 5% $CO_2$, following manufacturer's instructions. Absorption reading at 450 nm (reference filter at 650 nm) was determined using MRX Revelation microtiter plate reader (Lab System). $CC_{50}$ values were defined as the compound concentration required for reducing cell viability by 50% as compared to the untreated control in absence of compound and was determined by non-linear fitting of compound dose-response data. Representative assay data can be found in Table II below:

TABLE II

| Compound # | GT-1a (EC50) (nM) | GT-1b (CC50) (µM) |
| --- | --- | --- |
| I-1 | 10.6 | |
| I-2 | 156 | |
| I-3 | 2.95 | |
| I-4 | 0.13 | 8.16 |
| I-5 | 0.92 | |
| I-6 | 1.5 | |
| I-7 | 1.1 | |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

The invention claimed is:
1. A compound of formula I or II

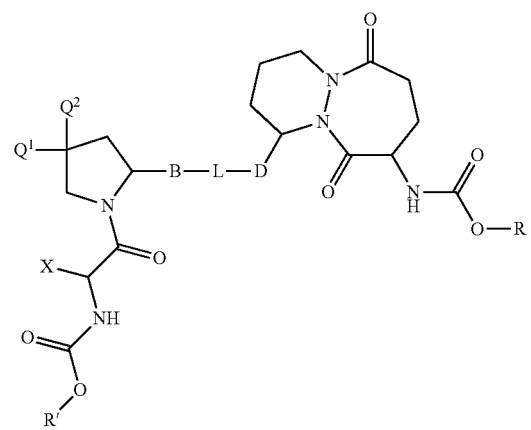

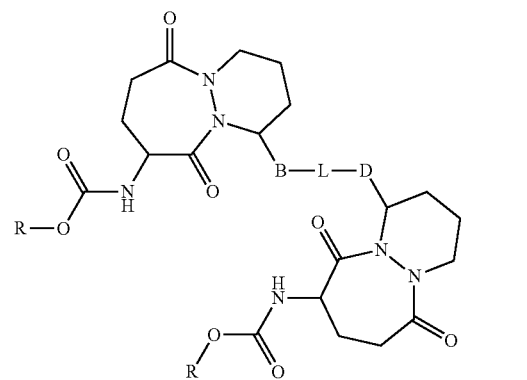

wherein:
X is lower alkyl;
each R is independently lower alkyl, or benzyl;
each R' is lower alkyl;
B and D are independently selected from the group consisting of

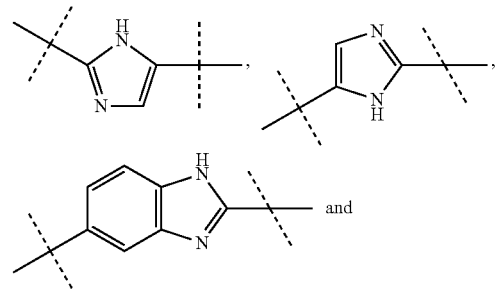

-continued

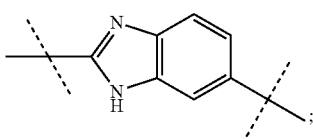

Q¹ and Q² are independently H or F;
or Q¹ and Q² together form heterocycloalkyl; and
L is

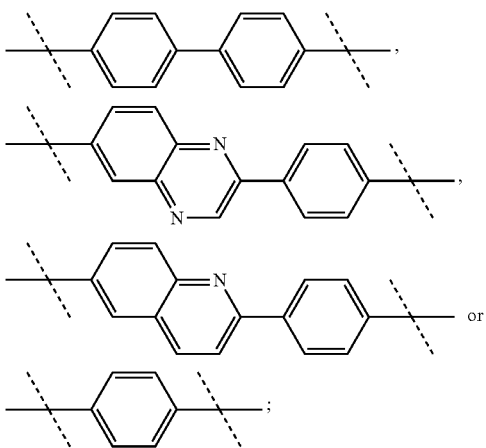

or a pharmaceutically acceptable salt thereof.

2. The compound of claim 1, wherein X is isopropyl.
3. The compound of claim 1, wherein R' is methyl.
4. The compound of claim 2, wherein R' is methyl.
5. The compound of claim 1, wherein R is methyl.
6. The compound of claim 2, wherein R is methyl.
7. The compound of claim 3, wherein R is benzyl.
8. The compound of claim 1, wherein R is benzyl.
9. The compound of claim 2, wherein R. is benzyl.
10. The compound of claim 3, wherein R is benzyl.
11. The compound of claim 1, wherein each R is methyl.
12. The compound of claim 2, wherein each R is methyl.
13. The compound of claim 1, wherein B is

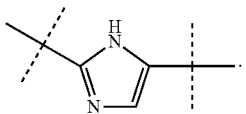

14. The compound of claim 2, wherein B is

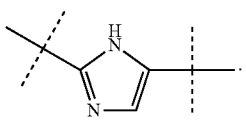

15. The compound of claim 3, wherein B is

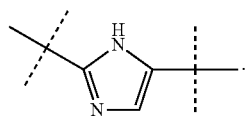

16. The compound of claim 4, wherein B is

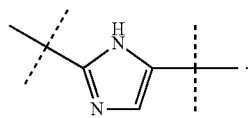

17. The compound of claim 5, wherein B is

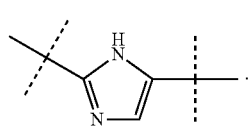

18. The compound of claim 6, wherein B is

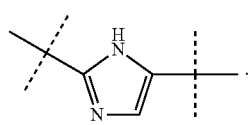

19. The compound of claim 7, wherein B is

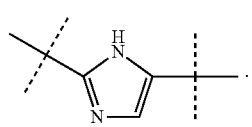

20. The compound of claim 8, wherein B is

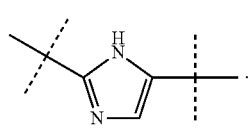

21. The compound of claim 9, wherein B is

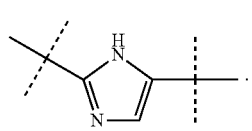

22. The compound of claim 10, wherein B is

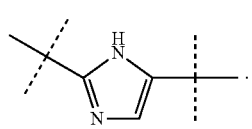

23. The compound of claim 11, wherein B is

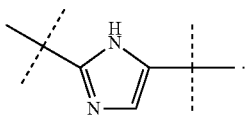

24. The compound of claim 12, wherein B is

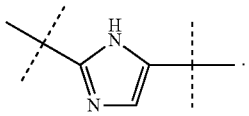

25. The compound of claim 1, wherein D is

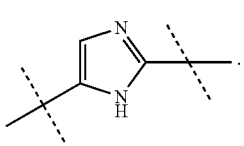

26. The compound of claim 1, wherein L is

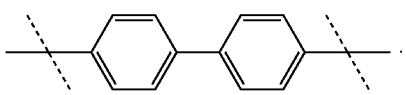

27. The compound of claim 1, wherein L is

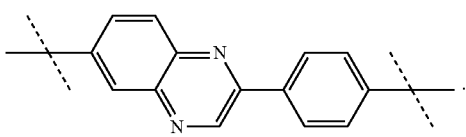

28. The compound of claim 1, wherein L is

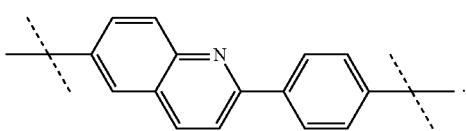

29. The compound of claim 1, wherein L is

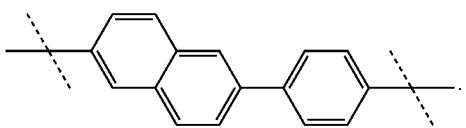

30. A compound selected from the group consisting of:

[(4S,7S)-4-(5-{4'-[2-((1S,9S)-9-[(Methoxycarbonyl)amino]-6,10-dioxo-octahydro-pyridazino[1,2-a][1,2]diazepin-1-yl)-3H-imidazol-4-yl]-biphenyl-4-yl}-1H-imidazol-2-yl)-6,10-dioxo-octahydro-pyridazino[1,2-a][1,2]diazepin-7-yl]-carbamic acid methyl ester;

{(4S,7S)-4-[5-(4-{2-[(S)-1-((S)-2-Methoxycarbonylamino-3-methyl-butyryl)-pyrrolidin-2-yl]-3H-imidazol-4-yl}-phenyl)-1H-benzoimidazol-2-yl]-6,10-dioxo-octahydro-pyridazino[1,2-a][1,2]diazepin-7-yl}-carbamic acid methyl ester;

{(4S,7S)-4-[5-(4'-{2-[(S)-1-((S)-2-Methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid benzyl ester;

((4S,7S)-4-{5-[4-(6-{2-[(S)-1-((S)-2-Methoxycarbonylamino-3-methyl-butyryl)-pyrrolidin-2-yl]-3H-imidazol-4-yl}-quinoxalin-2-yl)-phenyl]-1H-imidazol-2-yl}-6,10-dioxo-octahydro-pyridazino[1,2-a][1,2]diazepin-7-yl)-carbamic acid methyl ester;

{(4S,7S)-4-[5-(4'-{2-[(S)-4,4-Difluoro-1-((S)-2-methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester;

{(4S,7S)-4-[5-(4'-{2-[2-((S)-2-Methoxycarbonylamino-3-methyl-butyryl)-8-oxa-2-aza-spiro[4.5]dec-3-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester; and {(4S,7S)-4-[5-(4'-{2-[(S)-1-((S)-2-Methoxycarbonylamino-3-methyl-butyryl)-pyrrolidin-2-yl]-3H-imidazol-4-yl}-biphenyl-4-yl)-1H-imidazol-2-yl]-6,10-dioxo-octahydro-pyridazino[1,2-a][1,2]diazepin-7-yl}-carbamic acid methyl ester.

31. A method for treating a Hepatitis C Virus (HCV) infection comprising administering to a patient in need thereof a therapeutically effective amount of a compound of claim 1.

32. The method of claim 31, further comprising administering an immune system modulator or an antiviral agent that inhibits replication of HCV, or a combination thereof.

33. The method of claim 32, wherein the immune system modulator is an interferon or chemically derivatized interferon.

34. The method of claim 32, wherein the antiviral agent is selected from the group consisting of a HCV protease inhibitor, a HCV polymerase inhibitor, a HCV helicase inhibitor, a HCV primase inhibitor, a HCV fusion inhibitor, and a combination thereof.

35. A method for inhibiting replication of HCV in a cell comprising administering a compound of claim 1.

36. A pharmaceutical composition, comprising a compound of claim 1 and a pharmaceutically acceptable excipient.

* * * * *